United States Patent [19]
TenHoff et al.

[11] Patent Number: 5,984,871
[45] Date of Patent: Nov. 16, 1999

[54] ULTRASOUND TRANSDUCER WITH EXTENDED FOCUS

[75] Inventors: Harm TenHoff, Mountain View; James D. Koger, Santa Cruz, both of Calif.

[73] Assignee: Boston Scientific Technologies, Inc., Maple Grove, Minn.

[21] Appl. No.: 08/909,577

[22] Filed: Aug. 12, 1997

[51] Int. Cl.⁶ ........................................... A61B 8/12
[52] U.S. Cl. .................. 600/459; 600/463; 600/472; 310/335; 310/336
[58] Field of Search ................... 600/459, 472; 73/642, 644; 310/334–336

[56] References Cited

U.S. PATENT DOCUMENTS

| | | | |
|---|---|---|---|
| 4,184,094 | 1/1980 | Kopel ........................................ | 310/335 |
| 4,205,686 | 6/1980 | Harris et al. ............................. | 600/459 |
| 4,462,092 | 7/1984 | Kawabuchi et al. ..................... | 367/105 |
| 4,503,861 | 3/1985 | Entrebiun ................................. | 73/642 |
| 4,686,408 | 8/1987 | Ishiyama ................................. | 310/334 |
| 4,841,977 | 6/1989 | Griffith et al. ......................... | 29/25.35 |
| 4,951,677 | 8/1990 | Crowley et al. ....................... | 128/662.06 |
| 5,042,493 | 8/1991 | Saito et al. .............................. | 600/459 |
| 5,095,911 | 3/1992 | Pomeranz ............................. | 128/662.06 |
| 5,123,418 | 6/1992 | Saurel et al. ............................ | 600/459 |
| 5,291,090 | 3/1994 | Dias ......................................... | 310/334 |
| 5,313,949 | 5/1994 | Yock ....................................... | 128/662.06 |
| 5,415,175 | 5/1995 | Honafy et al. ........................... | 600/459 |
| 5,417,219 | 5/1995 | Takamizawa et al. ................... | 600/459 |
| 5,423,319 | 6/1995 | Seyed-Bolorforosh ................. | 600/459 |
| 5,438,999 | 8/1995 | Kikuchi et al. ......................... | 128/662.03 |
| 5,596,989 | 1/1997 | Morita .................................... | 600/462 |
| 5,638,822 | 6/1997 | Seyed-Bolorforosh et al. ..... | 128/662.03 |
| 5,640,961 | 6/1997 | Verdonk ................................. | 600/459 |
| 5,660,180 | 8/1997 | Molinowski et al. .................. | 600/463 |
| 5,678,554 | 10/1997 | Hossach et al. ........................ | 600/459 |
| 5,704,361 | 1/1998 | Seward et al. .......................... | 600/463 |
| 5,834,687 | 11/1998 | Talbot et al. ............................ | 600/459 |
| 5,846,205 | 12/1998 | Curley et al. ........................... | 600/472 |

FOREIGN PATENT DOCUMENTS 7-59769  7/1995  Japan .

*Primary Examiner*—Francis J. Jaworski
*Attorney, Agent, or Firm*—Lyon & Lyon LLP

[57] ABSTRACT

An ultrasound transducer having an extended focus for enabling an ultrasound imaging catheter to image features at a distance from the transducer with a high resolution and a high penetration depth. The ultrasound transducer is configured such that the acoustic path-length from the periphery of the transducer is increased relative to the acoustic path-length from the center of the transducer thereby increasing the transition length and focal length of the transducer. The ultrasound transducer may include an acoustic element having a convex surface on a side which transmits and receives ultrasound waves. An acoustic backing material may be attached to the acoustic element opposite the side where ultrasound waves are transmitted and received, and an acoustic matching layer may be provided on the convex surface of the acoustic element. The acoustic matching layer may have a substantially uniform thickness such that it also has a convex outer surface. The radius of curvature of the convex surface of the acoustic transducer element will determine the focal length for a given size and frequency of operation of the ultrasound transducer.

24 Claims, 23 Drawing Sheets

| CONVEX CRYSTAL TO EXTEND FOCAL LENGTH | | | | | |
|---|---|---|---|---|---|
| frequency | 9000000 Hz | | low freq | 6750000 Hz | |
| bandwidth | 50% | | mlow freq | 7875000 Hz | |
| OD | 1.9304 mm | | cent freq | 9000000 Hz | |
| c | 540000 mm/s | | mhig.freq | 10125000 Hz | |
| | | | high freq | 11250000 Hz | |
| radius R mm | zR[mm] cent freq | zR[mm] low freq | zR[mm] high freq | s mm | s in lambda |
| 1 | -1.225 | -1.32432 | -1.19512 | 0.4658 | 2.722 |
| 5 | -61.2455 | 22.27352 | -27.2214 | 0.0932 | 0.545 |
| 6 | 58.80416 | 12.78287 | -293.908 | 0.0776 | 0.454 |
| 7 | 24.50072 | 9.800154 | 49.00257 | 0.0665 | 0.389 |
| 8 | 17.04383 | 8.340537 | 26.13406 | 0.0582 | 0.340 |
| 9 | 13.78148 | 7.474666 | 19.17431 | 0.0518 | 0.303 |
| 10 | 11.95139 | 6.901485 | 15.80672 | 0.0466 | 0.272 |
| 11 | 10.78014 | 6.494044 | 13.82072 | 0.0423 | 0.247 |
| 12 | 9.966221 | 6.189535 | 12.51081 | 0.0388 | 0.227 |
| 13 | 9.367753 | 5.953328 | 11.58196 | 0.0358 | 0.209 |
| 14 | 8.909186 | 6.764759 | 10.88902 | 0.0333 | 0.195 |
| 15 | 8.546599 | 5.610739 | 10.35223 | 0.0311 | 0.182 |
| 20 | 7.480983 | 5.130932 | 8.828912 | 0.0233 | 0.136 |
| 30 | 6.651637 | 4.726724 | 7.696398 | 0.0155 | 0.091 |
| 40 | 6.302299 | 4.547597 | 7.232528 | 0.0116 | 0.068 |
| 50 | 6.109771 | 4.446493 | 6.980109 | 0.0093 | 0.054 |
| 1E+15 | 5.44448 | 4.08336 | 6.12504 | 0.0000 | 0.000 |

FIG. 14

| DEFOCUSING LENS TO EXTEND NEAR FIELD OF LOW FREQUENCY TRANSDUCER ||||||||
|---|---|---|---|---|---|---|---|
| CONVEX LENS | | | | | | | |
| cent. freq. | 9000000 Hz | | | | low freq | 6750000 Hz | |
| bandwidth | 50% | | | | mlow freq | 7875000 Hz | |
| OD | 1.9304 mm | | | | cent freq | 9000000 Hz | |
| c1 | 2000000 mm/s = sound velocity in lens | | | | mhig.freq | 10125000 Hz | |
| c2 | 1540000 mm/s = sound velocity in water/blood | | | | high freq | 11250000 Hz | |
| radius R mm | zR[mm] cent freq | zR[mm] low freq | zR[mm] high freq | s mm | s in lambd 1 | in lambd 2 | |
| 1 | -21.5853 | 67.13052 | -12.0392 | 0.4658 | 2.096 | 2.722 | |
| 2 | 14.56192 | 7.698445 | 31.31085 | 0.2329 | 1.048 | 1.361 | |
| 3 | 9.345305 | 5.944254 | 14.23059 | 0.1553 | 0.699 | 0.908 | |
| 4 | 7.925672 | 5.336283 | 11.18095 | 0.1165 | 0.524 | 0.681 | |
| 5 | 7.263627 | 5.027744 | 9.90709 | 0.0932 | 0.419 | 0.545 | |
| 10 | 6.223849 | 4.506608 | 8.068563 | 0.0466 | 0.21 | 0.272 | |
| 20 | 5.808136 | 4.254557 | 7.383462 | 0.0233 | 0.105 | 0.136 | |
| 30 | 5.681637 | 4.215324 | 7.180238 | 0.0155 | 0.07 | 0.091 | |
| 40 | 5.620432 | 4.18154 | 7.082764 | 0.0116 | 0.052 | 0.068 | |
| 50 | 5.584338 | 4.161528 | 7.02554 | 0.0093 | 0.042 | 0.054 | D^2/4*lambda |
| 1E+15 | 5.44448 | 4.08336 | 6.8056 | 0 | 0 | 0 | 5.44 mm |

FIG. 15

.076 OD Flat vs. .076x5mm Spherical Radius Len
Flat    Lens
α 2.1° vs. 1.66°

$$\tan \alpha = \frac{19.5/\beta \times .6}{12/\theta 3 \; g \times 2^{3} \cdot 36} = .02g$$

$$\tan \alpha = \frac{}{\alpha 2 \; 2066} => \alpha$$

$Z_f = 36.5/Q \times \rho .52 d/D$
$\quad = 10.86 \text{ mm}$ $Z_f = \text{measured } 5.87$ $Z_f = \text{theo. } 0.8 \, D^2/4\lambda =$

| | SOLIDS AND EPOXIES | VENDOR | $V_L$ | $V_S$ | $\rho$ | $z$ | $\sigma$ | LOSS |
|---|---|---|---|---|---|---|---|---|
| AS | DKR332, 15phr mpda, 25phr LP3, 76C cure | D, E, T | 2.55 | 1.1 | 1.24 | 3.16 | 0.36 | 7.4 @ 1.3 |
| AS | DKR332, 15phr mpda, 30phr LP3, 80C cure | D, E, T | 2.66 | | 1.24 | 3.3 | | 0.0 @ 2 |
| AS | DKR332, 15phr mpda, 50phr alumina, 50C cure | B, D, E | 2.8 | 1.43 | 1.48 | 4.18 | 0.32 | |
| AS | DKR332, 15phr mpda, 60phr alumina, 50C cure | B, D, E | 2.78 | 1.45 | 1.54 | 4.27 | 0.31 | |
| AS | DKR332, 15phr mpda, SIC, r5 | C, D, E | 3.9 | | 2.24 | 5.74 | | |
| AS | DKR332, 15phr mpda, SIC, 25phr LP3, r5 | C, D, E, T | 3.75 | | 2.15 | 5.06 | | |
| AS | DKR332, 15phr mpda, 6 micron W, r5 | C, D, E | 1.75 | | 6.45 | 11.3 | | |
| AS | DKR332, 50phr V140, rt cure | E, GM | 2.34 | 0.97 | 1.13 | 2.64 | 0.4 | |
| AS | DKR332, 64phr V140, rt cure | E, GM | 2.36 | | 1.13 | 2.65 | | |
| AS | DKR332, 75phr V140, rt cure | E, GM | 2.35 | | 1.12 | 2.62 | | |
| AS | DKR332, 100phr V140, rt cure | E, GM | 2.22 | | 1.1 | 2.55 | | |
| AS | DKR332, 100phr V140, 30phr LP3, r6 | E, GM, T | 2.27 | | 1.11 | 2.55 | 7.5 | 2, 11.2 @ 2.5 |
| AS | DKR332, 100phr V140, 30phr LP3, r9 | E, GM, T | 2.36 | | 1.16 | 2.74 | | 9.6 @ 2 |
| AS | DKR332, 100phr V140, 50phr LP3, r8 | E, GM, T | 2.12 | | 1.11 | 2.63 | | 12.0 @ 2 |
| AS | DKR332, 50phr V140, 50phr St. Rolens Ash, 60C | E, GM, T | 2.43 | | 1.94 | 6.24 | | |
| CRC | Duraluminin 175 | | 6.32 | 3.13 | 2.72 | 17.63 | 0.34 | |
| AS | Duxscal | JM | 1.49 | | 1.68 | 2.5 | | 13.3 @ 0.5 |
| AS | K.por.e glue, EPX-1 or EPX-2, 100phA of n | Loc | 2.44 | | 1.1 | 2.68 | | 8.4 @ 5 |
| AS | Eccoeorb CR 124 | E | 2.52 | | 4.58 | 12.01 | | 9.4 @ 5 |
| | Epon A2S mpda | Sh, D | 2.625 | 1.23 | 1.21 | 3.4 | 0.45 | |
| | Epotek 301 | Wa | 2.64 | | 1.08 | 2.85 | | |
| | Epotek 330 | Wa | 2.57 | | 1.14 | 2.94 | | |
| | Epoteck H70S | Wa | 2.51 | | 1.58 | 4.88 | | |
| AS | Epoteck V6, 10phA of B, r6 | Wa | 2.61 | | 1.23 | 3.21 | | 4.5 @ 2 |
| AS | Epoteck V6, 10phA of B, r7 | Wa | 2.55 | | 1.23 | 3.14 | | 5 @ 2 |
| AS | Epoteck V6, 10phA of B, 20phA LP3, r6 | Wa, T | 2.6 | | 1.25 | 3.25 | | 5 @ 2 |
| AS | Epoteck V6, 10phA of B, 20phA LP3, r7 | Wa, T | 2.55 | | 1.26 | 3.22 | | 6 @ 2 |
| DIMA | Fused silicon | Dyna | 5.7 | 3.75 | 2.2 | 12.55 | 0.17 | 5.2 @ -5 @ 2 |
| M | Germanium, mp=937.4C, transparent to infared | C | 5.41 | | 5.47 | 29.6 | | |
| | Glass corning 0215 sheet | Corn | 5.66 | | 2.48 | 14.08 | | |
| | Glass, crown | MC | 5.1 | 2.8 | 2.24 | 11.4 | 0.28 | |
| | Glass, FK3 | Schott | 4.91 | 2.05 | 2.25 | 11.1 | 0.245 | |
| | Glass, FK6    large minimum oreder | Schott | 4.43 | 2.54 | 2.28 | 10.1 | 0.25 | |
| AK | Glass, flint | | 4.5 | | 3.6 | 16 | | |
| | Glass, wscor machinable code 965S | Lee | 5.51 | | 2.54 | 14 | | |
| | Glass, pyrex | Corn | 5.64 | 3.28 | 2.24 | 13.1 | 0.24 | |
| AK | Glass, quartz | | 5.5 | | 2.2 | 12 | | |
| AK | Glass, silicon | | 5.2 | | 2.2 | 13 | | |
| | Glass, soda lime | | 6 | | 2.24 | 13.4 | | |
| | Glass, TIK | Schott | 4.38 | | 2.38 | 10.5 | | |
| XE | Glucose | | 3.2 | | 1.55 | 5 | | |
| CMC | Gold, hard drawn | | 3.24 | 1.2 | 19.7 | 63.8 | 0.42 | |
| EM | Granite | | 6.5 | | 2.7 | 17.6 | | |
| M | Hsinium, mp-2150C, used in reactor control rods | C | 3.84 | | 13.28 | 51 | | |
| | Hydrogen, solid at 4.2K | | 2.15 | | 0.082 | 0.15 | | |
| AS | Hysol CAW795725 par hw796 50C | H | 2.7 | | 1.12 | 3.19 | | 17.0 @ 5 |
| HE | Hysol CS-4143/3404 | H | 2.65 | | 1.52 | 4.52 | | |
| HE | Hysol CS-4183/3561 | H | 2.92 | | 1.42 | 4.2 | | |
| HE | Hysol CS-4183/3561, 15pha CSW | M, Li | 2.52 | | 1.2 | 4.7 | | |
| HE | Hysol CS-4183/3561, 30pha CSW | M, Li | 2.42 | | 2.14 | 5.33 | | |
| HE | Hysol CS-4183/3561, 45pha CSW | M, Li | 2.3 | | 2.65 | 6.1 | | |
| HE | Hysol CS-4183/3561, 57.5pha CSW | M, Li | 2.18 | | 1.27 | 7.04 | | |
| AS | Hysol XK-0067/H-3719 76C formerly C9-H905 | M | 2.53 | | 1.23 | 4.85 | | 23.4 @ 5 |

FIG. 20a

| | SOLIDS AND EPOXIES | VENDOR | $V_L$ | $V_s$ | $\rho$ | $z$ | $\sigma$ | LOSS |
|---|---|---|---|---|---|---|---|---|
| | Steel, Stainless 347, Zs = 24.5 | | 5.78 | 3.1 | 7.89 | 45.7 | 0.3 | |
| | Stycast 1264, rz cure | EC | 2.22 | | 1.19 | 2.64 | | |
| RLB | Stycast 1264, 45pha, 600pha W, r5 | EC, C | 1.65 | | 4.71 | 2.92 | | 29.7 @ 5 |
| RLB | Stycast 1264, 45pha, 800pha W, r6 | EC, C | 1.57 | | 5.5 | 8.65 | | 46.5 @ 5 |
| RLB | Stycast 1264, 45pha, vac. Inpreg. w, rt | EC, C | 1.71 | | 6.03 | 10.4 | | 34.1 @ 5 |
| | Stycast 1267 | EC | 2.57 | | 1.16 | 3 | | 4.5 @ 3.* |
| JA | Stycast 1970, costs $109.00/lb | EC | 3.2 | | 1.9 | 5.08 | | |
| AS | Sycast 2651-40 9phar cat 9 rt cure | EC | 2.77 | | 1.5 | 4.16 | | |
| AS | Sycast 2651-40 9phar cat, 10phr SIC | EC, C | 2.55 | | 1.57 | 4.53 | | |
| AS | Sycast 2651-40 9phar cat, 20phr SIC | EC, C | 2.25 | | 1.63 | 4.82 | | |
| AS | Sycast 2651-40 9phar cat, 25phr SIC | EC, C | 2.9 | 1.5 | 1.57 | 4.81 | 0.32 | |
| | Sycast 2741, 1:1 | EC | 2.29 | | 1.17 | 2.68 | | |
| H | Sulphur, 9 isotropic forms exist, up approx 112C | | 1.35 | | 2 | 2.7 | | |
| H | Tantalum, mp=2995C, very inert, hard | C | 4.1 | 2.99 | 16.6 | 54.5 | | |
| AS | Tapox epoxy | Tsp | 2.48 | | 1.11 | 2.76 | | |
| AS | Techform EA700, brittle material | Tech | 2.63 | | 1.2 | 3.14 | 4.6 | 2, 5.2 @ 2.5 |
| | Teflon | | 1.19 | | 2.14 | 2.97 | 0.13 | 3.9 @ 5 |
| M | Thorium, mp=1700C, fissionable, high melting oxide | | 2.4 | 1.56 | 11.1 | 33.2 | 0.31 | |
| | Tin | | 3.1 | 1.7 | 7.3 | 24.2 | 0.32 | |
| | Titanium, mp1725C | | 6.1 | 3.1 | 4.48 | 27.3 | | |
| M, FK | Titanium carbide, mp3140C | C | 5.27 | 5.16 | 5.15 | 42.6 | | |
| | Tracon 401 ST | Tr | 2.97 | | 1.52 | 4.82 | | |
| | Tracon 2135 D | Tr | 2.45 | | 1.03 | 2.52 | | |
| | Tracon 2143 D | Tr | 2.37 | | 1.05 | 2.5 | | |
| | Tracon 2162 D | Tr | 2.02 | | 1.13 | 2.41 | | |
| | Tracon 3011 | Tr | 2.12 | | 1.2 | 2.54 | | |
| | Tungsten | C | 5.5 | 2.9 | 19.4 | 101 | 0.27 | |
| | Unabtainium | Proprietary | | | | | | |
| | Uranium | C | 3.4 | 2 | 18.5 | 63 | 0.24 | |
| M | Uranium dioxide | C | 5.18 | | 10.96 | 56.7 | | |
| M | Vanadium, mp 1890C | C | 6 | 2.78 | 6.03 | 36.2 | 0.36 | |
| PK | Wood, balsa | | 0.8 | | 0.1 | 0.08 | | Q = 1.5 |
| XF | Wood, cork | | 0.5 | | 0.24 | 0.12 | | |
| PK | Wood, cork | | 1.15 | | 0.13 | 0.15 | | Q = 2.0 |
| XF | Wood, oak | | 4 | | 0.72 | 2.9 | | |
| XF | Wood, pine | | 3.5 | | 0.45 | 1.57 | | |
| | Zinc, often very granular | | 4.2 | 2.4 | 7 | 29.5 | 0.25 | |
| | Zinc, oxide | | 6.4 | 2.85 | 5.68 | 36.4 | 0.37 | |
| M | Xiroaloy | | 4.72 | 2.35 | 9.36 | 44.2 | | |
| M | Zironium, mp=1852C, used in poison ivy lotion | C | 4.65 | 2.25 | 6.48 | 30.1 | 0.35 | |

FIG. 20b

| | RUBBERS | VENDOR | Vl | ρ | z | LOSS |
|---|---|---|---|---|---|---|
| | Adiprene LW-520 | Uni | 1.68 | 1.16 | 1.94 | |
| | Butyl rubber | | 1.90 | 1.11 | 2.00 | |
| AS | Dow Silastic Rubber GP45, 45 Durometer | MPC | 1.02 | 1.14 | 1.15 | 23.4@4 |
| AS | Dow Silastic Rubber GP75, 75 Durometer | MPC | 1.04 | 1.25 | 1.30 | 33.7@4 |
| AS | Ecogel 1265, 100PHA OF E, outgass, 80C | EC | 1.56 | 1.10 | 2.15 | 33.4@2 |
| AS | Ecogel 1256, 100PHA Of E, 100PHA Alumina, E4 | EC, B | 1.70 | 1.40 | 2.38 | >24.0@1.3 |
| AS | Ecogel 1256, 100PHA Of E, 1940PHA T1167, E4 | EC, C | 1.32 | 9.19 | 12.15 | 14@0.4 |
| | Ecothene CPC-39 | BC | 1.53 | 1.06 | 1.63 | |
| | Ecothene CPC-41 | BC | 1.52 | 1.01 | 1.54 | |
| | Neoprene | | 1.60 | 1.31 | 2.10 | 32.0@5 |
| AS | Fellathane, Tharmoplastic urethane Rubber 55 D Durometer | Upj | 2.18 | 1.20 | 2.62 | 45.1@4 |
| | Polyurethane, CC1090 | Gail | 1.76 | 1.11 | 1.96 | |
| AS | Polyurethane, HP-6400 | REM | 1.50 | 1.04 | 1.56 | |
| BB | Polyurethane, HP-6401 | REM | 1.63 | 1.07 | 1.74 | |
| BB | Polyurethane, HP-6402 | REM | 2.77 | 1.08 | 1.91 | |
| BB | Polyurethane, HP-6403 | REM | 1.87 | 1.10 | 2.05 | |
| BB | Polyurethane, HP-6405 | REM | 2.05 | 1.30 | 2.35 | |
| BB | Polyurethane, HP-6410 | REM | 1.33 | 1.04 | 1.38 | |
| BB | Polyurethane, HP-6413 | REM | 1.65 | 1.04 | 1.71 | |
| BB | Polyurethane, HP-6416 | REM | 1.78 | 1.05 | 1.86 | |
| BB | Polyurethane, HP-6422 | REM | 1.60 | 1.04 | 1.66 | |
| AS | PS-1201-Q (MEDIUM), PHR 10, RT Cure | PRC | 1.45 | 1.79 | 2.59 | 12.2@2 |
| | RTV-11 | GE, RS | 1.05 | 1.18 | 1.24 | 2.5@0.8 |
| | RTV-21 | GE, RS | 1.01 | 1.11 | 1.32 | 2.6@0.8 |
| | RTV-30 | GE | 0.97 | 1.45 | 1.41 | 2.6@0.8 |
| | RTV-41 | GE, RS | 1.01 | 1.31 | 1.32 | 3.2@0.8 |
| | RTV-60 | GE, RS | 0.96 | 1.47 | 1.41 | 2.8@0.8 |
| AS | RTV-60/0.5% DBT @ 5.00 MHZ | GE, RS | 0.92 | 1.49 | 1.37 | 34.0@5.00 |
| AS | RTV-60/0.5% DBT @ 2.25 MHZ | GE, RS | 0.92 | 1.49 | 1.37 | 11.5@2.25 |
| AS | RTV-60/0.5% DBT @ 1.00 MHZ | GE, RS | 0.92 | 1.49 | 1.37 | 3.65@1.00 |
| AS | RTV-60/0.5% DBT @ 5.00 MHZ/10 PHR TOLUEME | GE, RS | 0.92 | 1.48 | 1.36 | 43.2@5.00 |
| AS | RTV-60/0.5% DBT @ 2.25 MHZ/10 PHR TOLUEME | GE, RS | 0.91 | 1.48 | 1.35 | 10.8@2.25 |
| AS | RTV-60/0.5% DBT @ 1.00 MHZ/10 PHR TOLUEME | GE, RS | 0.91 | 1.48 | 1.35 | 3.76@1.00 |
| AS | RTV-60/0.5% DBT @ 2.25 MHZ/ 5 PHR VITREOUS C | GE, RS, A | 0.94 | 1.49 | 1.41 | 22.2@2.25 |
| AS | RTV-60/0.5% DBT @ 2.25 MHZ/10 PHR VITREOUS C | GE, RS, A | 0.95 | 1.51 | 1.45 | 13.1@2.25 |
| AS | RTV-60/0.5% DBT @ 1.00 MHZ/13.6 PHR W, Ril | GE, RS, C | 0.86 | 1.68 | 1.44 | |
| AS | RTV-60/0.5% DBT @ 1.00 MHZ/21.2 PHR W, Ril | GE, RS, C | 0.83 | 1.67 | 1.55 | |
| AS | RTV-60/0.5% DBT @ 1.00 MHZ/40.5 PHR W, Ril | GE, RS, C | 0.80 | 2.04 | 1.64 | |
| AS | RTV-60/0.5% DBT @ 1.00 MHZ/69.5 PHR W, Ril | GE, RS, C | 0.72 | 2.35 | 1.73 | |
| AS | RTV-60/0.5% DBT @ 1.00 MHZ/65.2 PHR W, Ril | GE, RS, C | 0.71 | 2.52 | 1.78 | |
| AS | RTV-60/0.5% DBT @ 1.00 MHZ/100.0 PHR W, Ril | GE, RS, C | 0.69 | 2.75 | 1.89 | |
| AS | RTV-60/0.5% DBT @ 1.00 MHZ/117.4 PHR W, Ril | GE, RS, C | 0.67 | 2.83 | 1.88 | |
| | RTV-77 | GE | 1.02 | 1.33 | 1.36 | 3.2@0.8 |
| | RTV-90 | GE | 0.96 | 1.50 | 1.44 | 4.2@0.8 |
| | RTV-112 | GE, RS | 0.94 | 1.05 | 0.99 | |
| | RTV-116 | GE, RS | 1.02 | 1.10 | 1.12 | |
| | RTV-118 | GE, RS | 1.03 | 1.04 | 1.07 | |
| | RTV-511 | GE, RS | 1.11 | 1.15 | 1.31 | 2.5@0.8 |
| AS | RTV-560, 0.6% DBT | GE, RS | 0.99 | 1.41 | 1.40 | 2.2@0.8, 8.4@2 |
| | RTV-577 | GE, RS | 1.06 | 1.35 | 1.46 | 3.8@0.8 |
| | RTV-602 | GE | 1.15 | 1.02 | 1.18 | 4.35@0.8 |
| | RTV-615, use with 455 primer | GE, RS | 1.06 | 1.02 | 1.10 | 1@0.8 |

FIG. 20c

| | LIQUIDS | VENDOR | $V_L$ | $\Delta V/\Delta X$ | $\rho$ | z | LOSS |
|---|---|---|---|---|---|---|---|
| M | Acetate, butyl | | 1.27 | | 0.571 | 1.02 | |
| M | Acetate, athyl, $C_4M_8O_2$ | | 1.15 | | 0.9 | 1.069 | |
| M | Acetate, mehtyl, $C_3H_6O_2$ | | 1.21 | | 0.934 | 1.131 | |
| M | Acetate, propyl | | 1.18 | | 0.091 | 1.05 | |
| LB | Acetone, $(CH_3)ZcCO$ at 25c | | 1.74 | -4.5 | 0.791 | 1.07 | A=54.0 |
| M | Acatanitrile, $C_2H_3N$ | | 1.29 | | 0.783 | 1.01 | |
| M | Acetonyl acatone, $C_6H_{10}O_2$ | | 1.4 | | 0.729 | 1.358 | |
| M | Acetylendichloride, $C_2H_2C_{12}$ | | 1.02 | | 1.26 | 1.26 | |
| M | Alcohol, butyl, $C_4H_9OH$ at 30C | | 1.24 | | 0.81 | 1.003 | A=74.3 |
| CRC | Alcohol, athanol, $C_2H_5OH$, at 25C | | 1.207 | -4 | 0.79 | 0.85 | A=48.5 |
| M | Alcohol, furfuryl, $C_5H_4O_2$ | | 1.45 | | 1.135 | 1.654 | |
| LB | Alcohol, isopropyl, z-Propanal, at 20C | | 1.17 | | 0.785 | 0.92 | A=82 |
| CRC | Alcohol, methanal, $CH_3OH$, at 25C | | 1.103 | -3.2 | 0.791 | 0.872 | A=30.2 |
| M | Alcohol, propyl (n) $C_3H_7OH$ at 30C | | 1.22 | | 0.904 | 0.863 | A=64.5 |
| M | Alcohol, t-amyl, $C_5H_9OH$ | | 1.2 | | 0.81 | 0.876 | |
| M | Alkazone 13, $C_{15}H_{24}$ | | 1.32 | | 0.86 | 1.132 | |
| M | Aniline, $C_6H_5MH_2$ | | 1.69 | | 1.022 | 1.675 | |
| DR | Argon, liquid at 87K | | 0.84 | | 1.43 | 1.2 | A=15.2 |
| CRC | Benzene, $C_6H_6$, at 25C | | 1.295 | -4.65 | 0.87 | 1.12 | A=572 |
| M | Benzol | | 1.33 | | 0.878 | 1.16 | |
| M | Benzol, ethyl | | 1.34 | | 0.868 | 1.18 | |
| | Bromobenzene $C_5H_5Br$ at 22C | | 1.167 | | 1.522 | 1.776 | A=1.63 |
| M | Bromoform, $CHBR_3$ | | 0.92 | | 2.89 | 2.07 | |
| M | t-Butyl chloride, $C_4H_9CL$ | | 0.98 | | 0.84 | 0.827 | |
| M | Butyrate, athyl | | 1.17 | | 0.877 | 1.03 | |
| M | Carbitol, $C_6H_{14}O_3$ | | 1.46 | | 0.966 | 1.432 | |
| CRC, H | Carbon disulphide, $CS_2$ at 25C | | 1.145 | | 1.26 | 1.448 | |
| DR | Carbon disulphide, $CS_2$ at 25C, 3 CRx | | 1.31 | | 1.221 | 1.85 | A=10.1 |
| CRC, H | Carbon Tectrachloride, $C(CL)_4$, at 25C | | 0.926 | -2.7 | 1.394 | 1.48 | A=538 |
| M | Casium at 28.5C the melting point | | 0.967 | | 1.88 | 1.82 | |
| La | Chloro-benzene, $C_6H_5Cl$, at 25C | | 1.304 | | 1.106 | 1.442 | A=157 |
| M | Chloro-benzene, $C_6H_5C$ | | 1.3 | | 1.1 | 1.432 | |
| CRC, M | Chloroform, $CHC_{13}$, at 25C | | 0.947 | -3.4 | 1.49 | 1.47 | |
| M | Cyclonaranal, $C_6H_{12}O$ | | 1.45 | | 0.962 | 1.4 | |
| M | Cyclohexazone, $C_6H_{10}O$ | | 1.42 | | 0.248 | 1.391 | |
| M | Diacmtyl, $C_4H_6O_2$ | | 1.23 | | 0.99 | 1.222 | |
| M | Dichoraizobutane (1, 3), $CH_{18}(CL)_2$ | | 1.22 | | 1.14 | 1.39 | |
| M | Diathyl katone | | 1.31 | | 0.812 | 1.07 | |
| M | Diamthyl phythalate, $C_9H_{10}O_4$ | | 1.46 | | 1.2 | 1.758 | |
| M | Dioxane | | 1.36 | | 1.033 | 1.423 | |
| CRC, M | Ethanol oxide, $C_2H_7C$, at 25C | | 1.724 | -3.4 | 1.018 | 1.755 | |
| CRC, M | Ethyl ether, $C_4H_{10}C$, at 25C | | 0.585 | -4.87 | 0.723 | 0.07023 | |
| M | d-Pexchane | | 1.32 | | 0.94 | 1.241 | |
| M | Florosilicone oil, Dow FE-12GE | | 0.76 | | | | |
| M | Formamide, $CH_3HO$ | | 1.52 | | 1.134 | 1.842 | |
| M | Furfural, $C_5H_4O_2$ | | 1.45 | | 1.157 | 1.67 | |
| 3m | Fluorinert FG-40 | 3m | 0.64 | | 1.86 | 1.19 | |
| 3m | Fluorinert FG-70 | 3m | 0.687 | | 1.94 | 1.22 | |
| 3m | Fluorinert FG-72 | 3m | 0.512 | | 1.86 | 0.86 | |
| 3m | Fluorinert FG-75 | 3m | 0.585 | | 1.76 | 1.02 | |
| 3m | Fluorinert FG-77 | 3m | 0.595 | | 1.78 | 1.05 | |
| 3m | Fluorinert FG-104 | 3m | 0.575 | | 1.76 | 1.01 | |
| 3m | Fluorinert FG-42 | 3m | 0.655 | | 1.85 | 1.21 | |

FIG. 20d

| | LIQUIDS | VENDOR | $V_L$ | $\Delta V/\Delta X$ | $\rho$ | z | LOSS |
|---|---|---|---|---|---|---|---|
| M | Oil, SAE 20 | | 1.74 | | 0.87 | 1.51 | |
| | Oil, SAE 30 | | 1.7 | | 0.88 | 1.5 | |
| JA | Oil, silicon Dow 200, 1 centistoke | DC | 0.8 | | 0.814 | 0.74 | |
| JA | Oil, silicon Dow 200, 10 centistoke | DC | 0.868 | | 0.94 | 0.91 | |
| JA | Oil, silicon Dow 200, 100 centistoke | DC | 0.98 | | 0.968 | 0.95 | |
| JA | Oil, silicon Dow 200, 1000 centistoke | DC | 0.99 | | 0.972 | 0.96 | |
| MH | Oil, silicon Dow 704 @ 79F | DC | 1.408 | | 1.02 | 1.437 | |
| MW | Oil, silicon Dow 704 @ 79F | DC | 1.458 | | 1.15 | 1.88 | |
| GD | Oil, silicon Dow 704 @ 20C | DC | 1.352 | | 1.11 | 1.5 | A=200 |
| JA | Oil, safflower | | 1.45 | | 0.9 | 1.3 | |
| JA | Oil, soybean | Wesson | 1.43 | | 0.93 | 1.32 | |
| M | Oil, sperm | | 1.44 | | 0.88 | 1.268 | |
| JA | Oil, sunflower | | 1.45 | | 0.92 | 1.34 | |
| M | Oil, transformer | | 1.38 | | 0.92 | 1.28 | |
| JA | Oil, wintergreen (methyl salicylate) | CVS | 1.38 | | 1.15 | 1.6 | |
| DR | Oxygen, $O_2$, liquid at 90K | | 0.5 | | 1.11 | 1.0 | A=9.9 |
| M | Paraffin at 15C | | 1.3 | | | | |
| | n-Pentane, $C_5H_{12}$, liquid at 15C | | 1.027 | | 0.626 | 0.642 | A=100 |
| M | Polypropylane oxide (Ambiflo) at 38C | | 1.37 | | | | |
| M | Potassium at 100C, mp=63.7C see "H" for other temps | | 1.82 | | 0.83 | 1.52 | |
| M | Pyridine | | 1.41 | | 0.282 | 1.38 | |
| M | Sodium, liquid at 300C, (see 'M' for other temps) | | 2.42 | | 8.81 | 21.32 | |
| M | Solvenne #3 | | 1.37 | | 0.877 | 1.202 | |
| AS | Sonotrack complant | Eche | 1.62 | | 1.04 | 1.68 | |
| M | Tallow at 16C | | 0.39 | | | | |
| M | Thallium at mp=303.5C, used in photocells | C | 1.62 | | 11.9 | 19.3 | |
| M | Trichorethylene | | 1.05 | | 1.05 | 1.1 | |
| CRC | Turpentine, at 25C | | 1.255 | | 0.88 | 1.104 | |
| M | Univis 800 | | 1.35 | | 0.87 | 1.132 | |
| M | Water, heavy, D20 | | 1.4 | | 1.104 | 1.54 | |
| M | Water, liquid at 20C | | 1.48 | | 1.00 | 1.483 | |
| CRC, DR | Water, liquid at 25C | | 1.4967 | 2.4 | 0.998 | 1.494 | A=22 |
| | Water, liquid at 30C | | 1.509 | | 1.00 | 1.509 | A=19.1 |
| DR | Water, liquid at 30C, temps up to 500F listed in 'CRC' | | 1.55 | | 1.00 | 1.55 | A=10.3 |
| M | Water, salt 10% | | 1.47 | | | | |
| M | Water, salt 15% | | 1.83 | | | | |
| M | Water, salt 20% | | 1.6 | | | | |
| CRC | Water, sea, at 25C | | 1.531 | 2.4 | 1.025 | 1.569 | |
| DR | Xerxum, liquid at 156K | | 0.63 | | 2.86 | 1.5 | A=22.0 |
| CRC, M | Xylene Hexafloride, $C_8H_4F_6$, at 25C | | 0.879 | | 1.37 | 1.222 | |
| M | a-Xylol, $C_8H_{10}$ | | 1.32 | | 0.064 | 1.145 | |

FIG. 20e

Vendor Abbreviations

| | |
|---|---|
| 3m | Bay Area, (425)257-2244, Los Angeles, (212)726-6305 |
| A | Atomargic Chemicals, 91 Carolyn Blvd., Farmingdale, WI 11735 (516)694-9000 |
| Acme | Acme Chemicals, PO Box 1404, New Haven, Conn. 04505, (203)562-2171 |
| AMD | AMD Engineering, Rockland, Ma. 02370 |
| Amer | American Hoechst Corp., Tustin, CA. (714)730-5051 |
| AMPL | AMPL Prochal, Paris, France |
| B | Brinkman Instruments Inc., Great Neck LI, NY |
| | Chemistry Stores, Stanford University, Stanford Ca. 94305, (414)497-1277 |
| Bacon | Bacon Industries, Inc., 15731 Hale Avenue, Irvine Ca 92714, (714)863-1499 |
| BFG | B.F. Goodrich, (216)374-4123 Howard Hochrad, Karen Bird, 500 S. Main St., Akron, Ohio 44318 |
| Borg | Borg Warner Chemicals Inc., International Center, Parkersburg, W. Va. 26101 (304)424-5411 |
| | Colocite Plastics Co., 101 Railroad Ave., Richfield N.J. 07657 |
| C | Cora, PO Box 1170, Milwaukee, WI 53301, (414)283-9800 |
| Ch | Chemtock, Hayward, Ca., (415)765-0330 |
| Ciba | Ciba-Armidite Products |
| Corn | Corning Glass Works, S. Tsaffs, Sunnyvale, Ca., (404)732-5050 |
| | Corning Glass , Corning, N.Y. |
| CVS | Local pharmacy |
| D | X.I. Dupont de Memours, N8533 Freon Products Div., Wilington, Del. 15898 (800)441-7525 |
| | Ventron Corp., Alpha Products, 2098 Pina St., San Leandro, Ca. 94577 |
| | Ventron Corp., Alpha Products, Denver, Mass., (617)777-1970x404 |
| DC | Dow Corning, (everything is silicon based) Fresno, Ca. (209)441-0201 |
| | K.H. Anderson, 136 Wolfe Rd., Sunnyvale, Ca. 94055 (404)736-6730 |
| | Bronell Xlectre Products (212)924-5000 |
| Dyna | Dynamil Corp., Cooper Rd., Berlin, N.J. 08009 (609)767-4600 |
| E | E.T. Worn Co., 541 66th Ave., Oakland, Ca. 94621, (415)568-2737 |
| | Dow Chemical |
| EBL | EBL, 21 Tolland St., East Hartford, Conn. 06108, (203)285-5428 |
| | Vernitron, 333 Forbes Rd., Bedford, Ohio 44146, (216)232-8600 |
| | Wolfe Engineering, (714)646-7214 |
| | Channel Industries, 839 Ward Dr., Santa Barbara, Ca. 93405, (805)267-0171 |
| | Transducer Products, Rt 63 North, Coshen, Conn., (203)491-3251 |
| Echo | Echo Labs, PO Box 552, Lewiston, Penn. 17044, (717)248-4883 |
| EC | Emeraon Commings, 604 W 182nd St., Gardena, Ca. 90248, (213)329-1147, (213)321-6650x33 |
| Fl | Flourocarbon Process Systems, 1432 S Allec St., PO Box 3640, Anaheim, Ca. 92803, (714)966-7330 |
| Gall | Gallagher Corp., 3966 Morrison Dr., Gesrome, IL. 60031 (312)249-3440 |
| GE | General Electric, Silicon Products, Waterford, N.Y. 12166, (518)237-3330 |
| | Electrical Specialty Co., 213 E. Harris Ave., So. San Francisco, Ca. (425)549-9611 |
| GEP | General Electric, 1700 E. Cale, City of Industry, Ca. 91745 |
| GM | X.V. Roberts and Associates, Palo Alto, Ca., (415)494-1671 |
| | X.V. Roberts and Associates, 8500 Steller Dr., Culver City, Ca. 90230 |
| | Hankel Corporation |
| | General Mills |
| H | Hysol Division, Dextar Corp., Olean, N.Y. 14760 |
| | Hysol Insulting Materials, 15051 E. Don Julian Rd., Industry, Ca. 91749, (213)968-6511, (415)687-4201 |
| I | Indum Corp., PO Box 269, Ution, N.Y. 13503, (517)797-1630 Telex 237363 |
| JM | Johns-Manville |
| | Electrical Materials Inc., San Antonio Rd., Palo Alto, Ca. (415)494-0400 |
| Kara | Karamoe Inc., 104 W. Church, Liston, Ind. 46149 |
| Kodak | Eastman Chemical Products Inc., Kingsport, Tenn. |
| Lee | Lee Plastics, 793 E. Pico Blvd., Los Angeles, Ca. 90021, (217)745-5984 |
| Li | Li Tungsten Co., 63 Harribkill Rd., Glencove, N.Y. 11543, (518)676-1314 |

FIG. 20f

ULTRASOUND TRANSDUCER WITH EXTENDED FOCUS

FIELD OF THE INVENTION

The present invention relates to intraluminal, intracavity, intravascular, and intracardiac ultrasound imaging catheters and more specifically to an ultrasound transducer having an extended focus.

BACKGROUND OF THE INVENTION

Ultrasound imaging catheters typically produce cross-sectional views of internal features of a living body to assist in accurate medical diagnosis and treatment decisions. Intravascular and intraluminal ultrasound imaging refers generally to imaging from within blood vessels, arteries, and other small lumens. Intracardiac imaging refers to imaging the walls of the heart. Ultrasound imaging catheters generally image features a short distance from the transducer.

Ultrasound imaging devices are generally known, and although there are various ways to accomplish this type of imaging, imaging catheters employ mechanisms to transmit scanning beams of ultrasound energy into the area being studied and to receive the return echoes from each scan in order to generate an image which can be seen on a visual display such as a monitor. The transmitted ultrasound beam has several important parameters, such as frequency, beam-width in the near-field and far-field, focal length, transition length between near and far-field, and beam intensity which define the performance characteristics of the ultrasound imaging system. Some of the most important performance characteristics of an ultrasound imaging system include axial and lateral resolution and penetration depth. The resolution of an ultrasound imaging system is defined as the minimum distance of separation between two objects and the maximum distance from the two objects at which the two objects can still be identified separately in the ultrasound image. The penetration depth is the depth below the surface of the feature at which the ultrasound waves can detect and produce an image.

Axial resolution and lateral resolution typically improve with increasing frequency. Increasing the frequency of a system, however, reduces the penetration depth of the ultrasound beam and consequently the depth of view. Hence, the optimal acoustic frequency for any given imaging application using conventional ultrasound transducers is a compromise between resolution and penetration depth. Reducing the beam diameter also improves lateral resolution. For an exhaustive discussion of ultrasound beam characteristics and the relationship of these characteristics to performance parameters, the reader is referred to Harm ten Hoff, "Scanning Mechanisms for Intravascular Ultrasound Imaging; A Flexible Approach"; ISBN:90-9006072-3; Ph.D. Thesis (1993); Erasmus University Rotterdam, The Netherlands; "Diagnostic Ultrasound; Principles and Instruments," 4th Ed., Frederick W. Kremkau, W. V. Saunders Co., Philadelphia, ISBN:0-7216-4308-6 (1993); these and all other references cited herein are expressly incorporated by reference as if fully set forth in their entirety herein.

The penetration depth of an ultrasound imaging system is a function of the frequency, the dynamic range of the system, and the ultrasound beam shape. Usually, however, the dynamic range is limited because excessive intensity can result in cavitation which can cause severe damage to the catheter and to the surrounding tissue. The penetration depth can be improved by optimizing the beam shape by extending the beam focal length and producing a tighter beam at a desired distance from the transducer. Hence, imaging system design aspects other than frequency may be changed to affect the beam shape thereby improving the resolution and penetration depth of the ultrasound imaging system.

In turn, the shape of an ultrasound beam of a single transducer is a function of the shape and dimensions of the transducer, the ultrasound frequency and the use of focusing. Referring to FIG. 1, a typical ultrasound beam-shape is described. The near-field extends from the transducer and is characterized by a converging beam and an irregular ultrasound intensity pattern due to interference of ultrasound waves originating from different parts of the transducer. In the near-field, the acoustic field amplitude and phase are erratic due to the constructive and destructive interference of energy emitted by different parts of the transducer. The near-field can be described as somewhat incoherent.

The transition from near-field to far-field conditions is located at a distance $Z=Z_R$ from the transducer. The transition length, $Z_R$, is defined as the distance from the transducer along the central axis of the transducer where the difference between the acoustic path-length from the center of the transducer and from the periphery of the transducer is one-half a wavelength (½λ). This can be better described with reference to FIG. 11 which depicts a transducer having a flat acoustic element 2 and no focusing lens. Throughout this application, "standard transducer" refers to a transducer having a flat acoustic element and no focusing lens. In FIG. 11, the lines b and $Z_R$ represent acoustic path-lengths. The acoustic path-length is measured from an iso-phasic (coherent) plane on or inside the transducer assembly, usually the front surface of the acoustic element. The acoustic path-length through a media can be expressed in the number of wavelengths and is equal to:

$$P_x = f \times \frac{L_x}{c_x}$$

where $L_x$=geometric path-length through media$_x$
$c_x$=speed of sound in media$_x$
f=acoustic frequency The distance b represents the acoustic path-length from the periphery of the transducer, and the distance $Z_R$ represents the acoustic path-length from the center of the transducer. The transition length, $Z_R$, is located at a distance from the transducer where:

$$b - Z_R = \frac{1}{2}\lambda$$

Using this definition, it can be seen that closer to the transducer, in the near-field, the difference, $b-Z_R$, is larger than ½λ. Conversely, further away from the transducer, in the far-field, the difference, $b-Z_R$, is smaller than ½λ, resulting in an increasingly coherent and diverging beam.

The far-field is distinguished by wavefronts (iso-phasic lines) which are convex-shaped and diverging. The natural focal point is located at the point of minimum beam width, $W_f$, which is at a distance from the transducer defined as the focal length, $Z_f$, generally about $0.8Z_R$ from the transducer surface.

According to the above definitions, $Z_R$ and the natural focal length $Z_f$ will increase when the acoustic path-length from the periphery of the transducer increases with respect to the acoustic path-length from the center of the transducer. Hence, increasing the diameter of the transducer will increase $Z_R$ and also $Z_f$. By the same principle, $Z_R$ and $Z_f$ can be decreased by decreasing the acoustic path-length from the periphery of the transducer with respect to the acoustic path-length from the center of the transducer.

An example of the effect of shortening $Z_R$ and $Z_f$ is seen in the known use of a concave lens to focus an ultrasound beam. Referring to FIG. 2, an ultrasound transducer comprises a flat acoustic element 2 having a concave lens 3 laid on the front of the acoustic element. $Z'_R$ and $Z'_f$ represent the transition length and focal length, respectively, of a standard transducer. The material of the lens is selected so that the speed of sound in the lens, $c_1$, is greater than the speed of sound in the medium (usually water/blood), $c_m$. Because the path, b, from the periphery travels a greater distance through the lens at a greater speed than the path, $a_R$, from the center, the acoustic path-length from the periphery of the transducer is decreased relative to the acoustic path-length from the center of the transducer to the transition point, $Z'_R$, of a same sized standard transducer. Accordingly, the transition length $Z_R$ and the focal length $Z_f$ are decreased relative to $Z'_R$ and $Z'_f$ for the transducer without the lens.

A similar effect can be observed when the acoustic path-length along the axis is shortened with respect to the acoustic path-length from the periphery. In other words, when a portion of the acoustic path-length along the axis is reduced, the remainder of the acoustic path-length must be increased, thereby increasing the transition length $Z_R$ to maintain the ½λ difference between the acoustic path-lengths from the periphery and from the center of the transducer.

As the beam travels through the near-field, its diameter decreases, and the beam is described as being tight. As the beam travels through the far-field, its diameter increases and the beam is described as diverging. This is true even for flat unfocused transducer elements because even for flat transducer elements there is some beam narrowing or "focusing." For a given transducer diameter, increasing the beam frequency increases the near-field length and produces a narrower beam. Reducing the beam diameter improves the lateral resolution. Therefore, lateral resolution is greatest at the focal point and decreases beyond the focal point as the beam travels through the far-field in a diverging pattern.

A larger transducer may also improve lateral resolution and penetration depth, but a larger transducer requires a larger catheter, and the catheter size may often be restricted by the size of the vessels through which it must fit.

As described above, with reference to FIG. 2, an ultrasound beam shape may also be adjusted by the use of focusing. Ultrasound waves have been disclosed to be focused by using a curved (rather than flat) transducer element, a curved reflector in the transducer assembly, or a lens. The emphasis of ultrasound imaging design has been concentrated on the ability to image smaller and smaller vessels in the distal regions of the coronary vasculature via a remote arterial site to obtain images of the vessel walls. This has been accomplished by inserting a catheter having an ultrasound transducer disposed on its distal end into a vessel and positioning the transducer proximate to the area of the vessel wall to be imaged. To be inserted into very small vessels, the size of the ultrasound transducer must be relatively small not only to traverse the vessels, but also to avoid occluding the vessel. Because the transducer is placed immediately adjacent or very close to the area to be imaged, a short focal length is required.

To this end, focusing has been used to converge the ultrasound beam for the purpose of shortening the focal length. For example, the ultrasonic transducer described in U.S. Pat. No. 5,438,999 to Kikuchi et al. includes a piezoelectric element having a concave surface to converge the ultrasonic beam, producing a shortened near-field and focal length and a tight beam in close to the transducer. A concave focusing device is used to shorten the focal length of the transducer in order to increase resolution and detection depth in close to the transducer. Kikuchi et al. also discloses an ultrasonic transducer having a convex acoustic lens made of silicone rubber materials for converging an ultrasonic beam. A convex lens made of silicone rubber materials will create a converging beam having a shortened focal length because the speed of sound in silicone (about 1 mm/μsec as shown in FIG. 19e tabulating materials and respective densities and speeds of sound) is slower than the speed of sound in the typical medium of water/blood (1.5 mm/μsec). Hence, the silicone rubber convex lens disclosed in Kikuchi et al. acts to increase the acoustic path-length along the center axis of the transducer with respect to the acoustic path-length from the periphery of the transducer, thereby decreasing the transition length, $Z_R$, and the focal length, $Z_f$.

However, the short focal lengths of the conventional flat and concave-shaped transducers limit the imaging distance from the transducer at which features may be imaged with good resolution and detection depth. These limitations restrict the type and size of internal features within the human body which may be imaged by systems utilizing these transducers. For instance, an ultrasound imaging catheter with a small enough diameter to insert intraluminally into the chambers of the heart may not have a large enough focal length to image the internal walls of the chambers with adequate resolution and detection depth.

More specifically, the maximum size catheter which can be inserted through the femoral artery to the left side of the heart is about 8F, and through the inferior vena cava to the right side of the heart is about 9F or 10F. A 9F catheter can accommodate a transducer up to a diameter of about 1.93 mm. Within the chambers of the heart, it is desirous to image a distance of up to 10 cm in order to image the walls of the heart. At a frequency of about 9 megahertz (MHz), which is needed for adequate penetration, the high resolution near-field for a flat transducer extends to only about 4.5 mm. Therefore, when the ultrasound beam reaches the walls of the heart chambers, the beam is well into the far-field where there is reduced resolution and penetration depth.

A need exists for an improved ultrasound transducer with an extended focus at low frequencies which can be used to image large chambers, organs, vessels, or other anatomic structures with high resolution and high penetration depth.

SUMMARY OF THE INVENTION

The present invention provides an ultrasound transducer having an extended focus thus enabling an ultrasound imaging catheter utilizing the transducer to image features at a distance from the transducer with a high resolution and high penetration depth. To accomplish this objective, the ultrasound transducer of the present invention comprises an acoustic unit configured such that the acoustic path-length from the periphery of the acoustic unit is increased with respect to the acoustic path-length from the center of the acoustic unit, or the acoustic path-length along the center axis of the acoustic unit is decreased with respect to the acoustic path-length from the periphery of the acoustic unit. Throughout this disclosure, the acoustic path-length is measured from the front surface of the acoustic element which generates ultrasound waves.

In another aspect of the present invention, the acoustic unit may comprise an acoustic element for transmitting and receiving ultrasound waves. The acoustic element will typically be bounded on one side by a backing layer and on the other side by a matching layer. The acoustic unit disclosed herein generates an acoustic wave which passes through the matching layer. In order to extend the transition length and consequently extend the focal length, the acoustic path-length from the periphery of the acoustic element is increased with respect to the acoustic path-length from the center of the acoustic element. Increasing the acoustic path-length from the periphery of the acoustic unit requires the transition length, $Z_R$, to extend in order to satisfy the ½λ difference in acoustic path-lengths from the periphery and the center which defines the transition length. As a result, the focal length, $Z_f$, is also extended. Alternatively, or in combination with extending the acoustic path-length from the periphery of the acoustic unit, the acoustic path-length from the center may be decreased with respect to the acoustic path-length from the periphery of the acoustic unit. This also results in increasing $Z_R$ and $Z_f$ similar to the effect of increasing the acoustic path-length from the periphery described above.

Increasing the transition length and focal length also causes the beam to have a narrower diameter and an extended near-field.

The acoustic transducer element in one embodiment therefore has a convex surface on a side which transmits and receives ultrasound waves. The radius of curvature of the convex surface is determined by the frequency of operation of the ultrasound transducer and the intended focal length. An acoustic backing material is attached to one side of the acoustic element opposite the side where ultrasound waves are transmitted and received. An acoustic matching layer is provided on the convex surface of the acoustic transducer element. In one embodiment, the acoustic matching layer has substantially uniform thickness such that it also has a convex outer surface. The convex-shaped elements form an acoustic unit having an acoustic path-length from the periphery of the acoustic unit which is increased relative to the acoustic path-length from the center of the acoustic unit. As stated above, this configuration creates a beam shape having a narrow diameter and an extended focal length. At the same time, the near-field is extended.

In another embodiment, the acoustic transducer element is configured to decrease the acoustic path-length from the center relative to the acoustic path-length from the periphery. This effect may be produced by a transducer having a substantially flat acoustic element and a convex lens. The lens may also perform the function of a matching layer. The material of the lens is chosen such that the speed of sound in the convex lens is greater than the speed of sound in the medium.

In still another embodiment, the focal length is extended by configuring the transducer with a concave acoustic element and an ellipsoidal-shaped lens, wherein the transducer is used in a surrounding acoustic medium characterized in that the speed of sound is higher in the lens than in the acoustic medium. Thus, the acoustic path-length from the center is decreased relative to the acoustic path-length from the periphery of the acoustic element, thereby extending the focus.

In yet another embodiment, the acoustic transducer comprises a flat acoustic element and a concave lens. The concave lens is made from a material such that the speed of sound in the lens is less than the speed of sound in the medium. Again, the acoustic path-length from the periphery of the acoustic unit which is increased relative to the acoustic path-length from the center of the acoustic unit, thereby extending the focus.

Accordingly, it is an object of the present invention to provide an ultrasound transducer. It is another object of the present invention to provide an ultrasound transducer with an extended focus. It is yet another object of the present invention to provide an ultrasound transducer with extended focus in order to obtain an ultrasound image of features at a distance from the transducer having high resolution and high penetration depth. It is a further object of the present invention to provide an ultrasound imaging catheter utilizing the ultrasound transducer with extended focus. It is another object of the present invention to provide an imaging guidewire utilizing the ultrasound transducer with extended focus.

BRIEF DESCRIPTION OF THE DRAWINGS

FIG. 3b is a cross-sectional view of the ultrasound transducer of FIG. 3a.

FIG. 14 is a table of theoretical calculated focal lengths of disk-shaped ultrasound transducer having a convex acoustic element and a matching layer of uniform thickness.

FIG. 15 is a table of theoretical calculated focal lengths of disk-shaped ultrasound transducer having a flat acoustic element and a convex acoustic matching layer.

FIGS. 20a–20f are tables of materials, densities, and speeds of sound.

DETAILED DESCRIPTION OF THE INVENTION

While the present invention is not to be bound by theory, it can be determined, both theoretically and empirically, that an ultrasound transducer modified to increase the acoustic path-length from the periphery of the transducer with respect to the acoustic path-length from the center of the transducer to the transition point, $Z'_R$, of a same sized standard transducer creates an ultrasound beam having an extended focal length and near-field and narrower beam compared to the same sized standard transducer. The same effect can be achieved when the acoustic path-length from the center of the transducer is decreased relative to the acoustic path-length from the periphery of the transducer. An extended focal length increases the distance from the transducer at which features can be imaged with high resolution and high penetration depth. This allows larger chambers, organs, and vessels to be effectively imaged.

The present invention is directed to an ultrasound transducer having an extended focus. To accomplish this, the ultrasound transducer is configured to increase the acoustic path-length from the periphery, or decrease the acoustic path-length from the center of the transducer, as the case may be.

Figure 1:
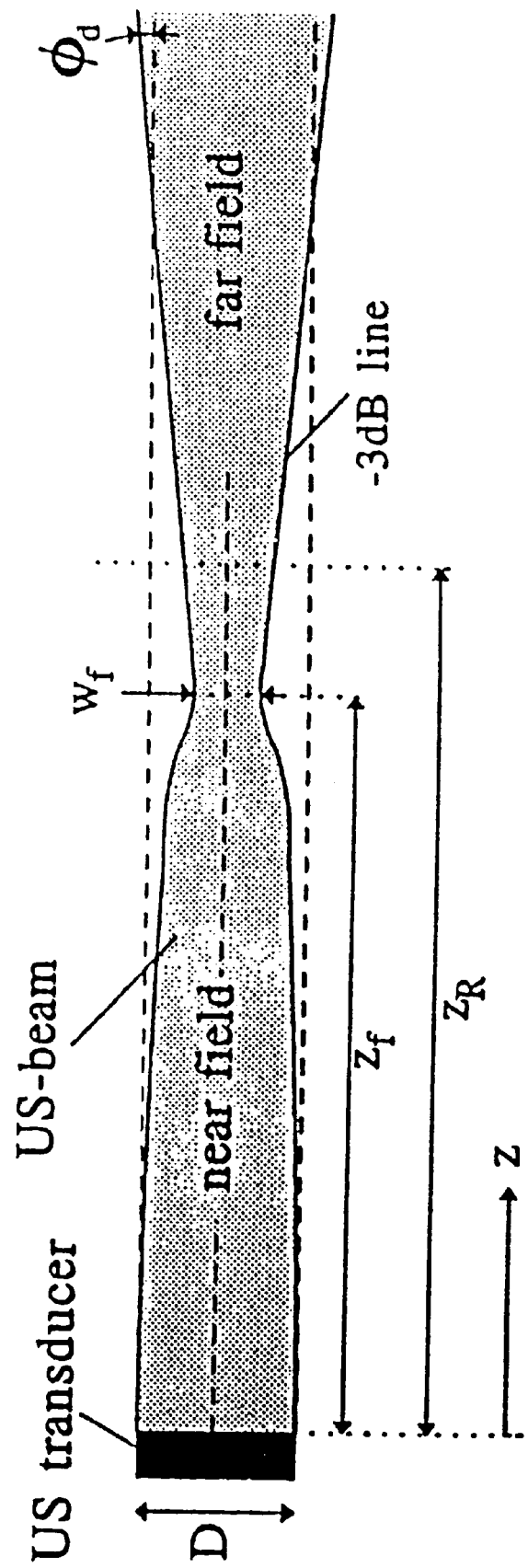
FIG. 1 illustrates an ultrasound beam and the parameters which characterize beam-shape.
Figure 2:
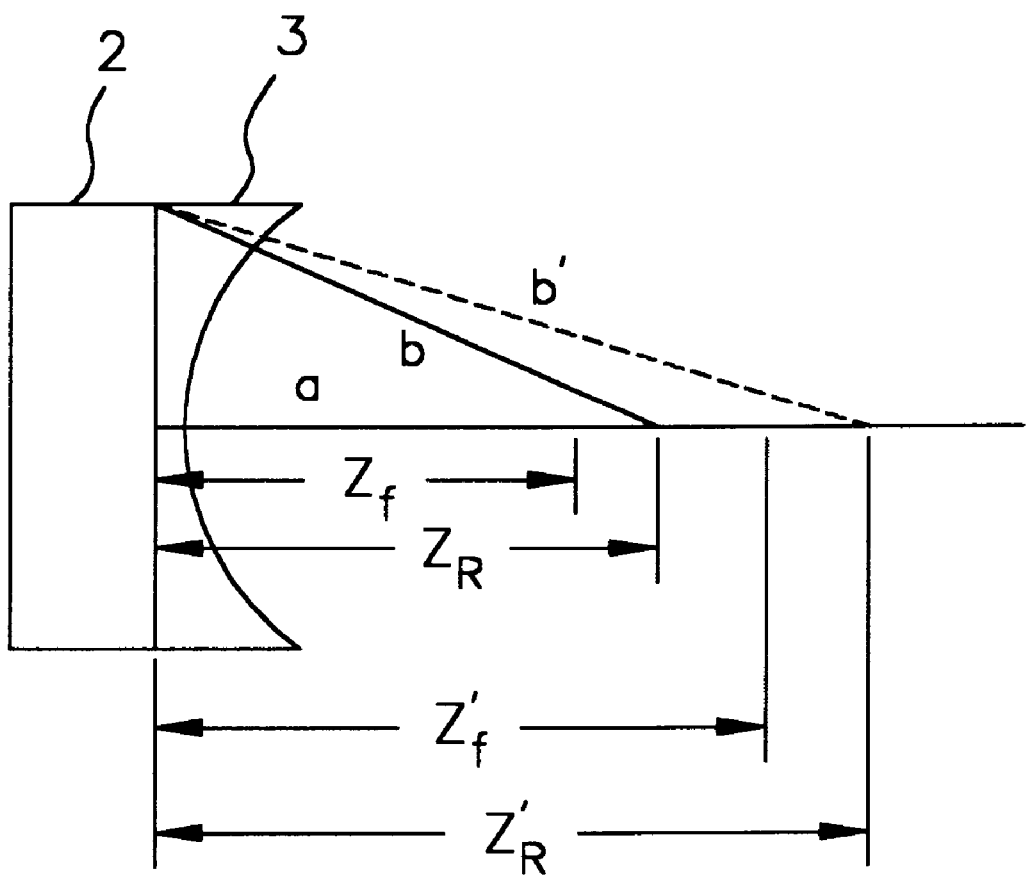
FIG. 2 is a schematic view of a transducer having a flat acoustic element and a concave lens.
Figure 3A:
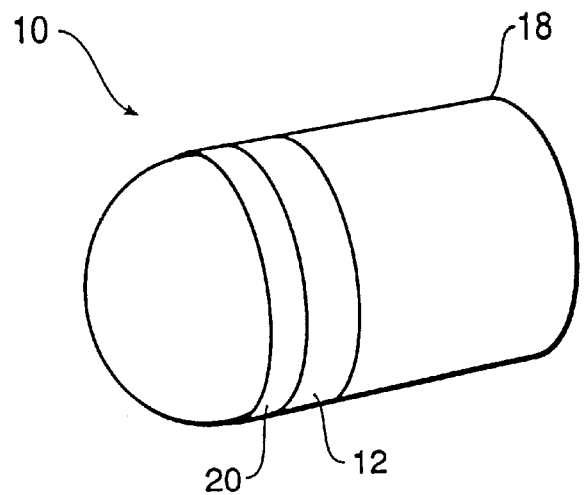
FIG. 3a is a perspective view of an ultrasound transducer in accordance with the present invention.
Figure 3B:
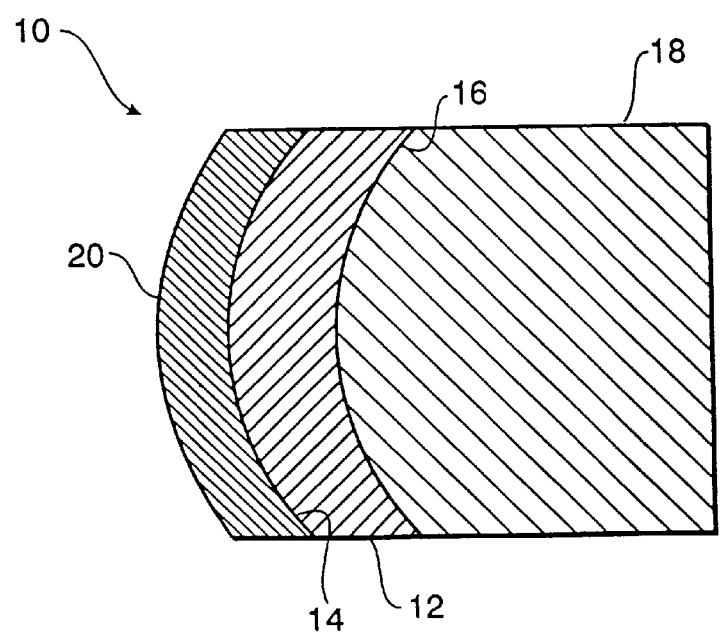

Referring to FIGS. 3a and 3b, a convex-surfaced, cylindrical ultrasound transducer 10 comprises an acoustic element 12 which may be a piezoelectric or piezostrictive material. The acoustic element 12 has a convex surface on the front side 14 from which ultrasonic waves are transmitted and received and a substantially uniform thickness such that the back side 16 of the acoustic element has a concave surface.

An acoustic backing 18 may be attached to the back side 16 of the acoustic element 12. The acoustic backing 18 is preferably made of a material having an attenuative nature to minimize the acoustic wave transmitted from the back side 16. An acoustic matching layer 20 is laid on the front side 14 of the acoustic element and, due to a substantially uniform thickness, matches the convex shape of front side 14. The acoustic impedance and thickness of the acoustic matching layer 20 depends on the environment or medium through which the ultrasound waves are to travel and the object to be imaged. This design choice is well known in the art.

Figure 4:
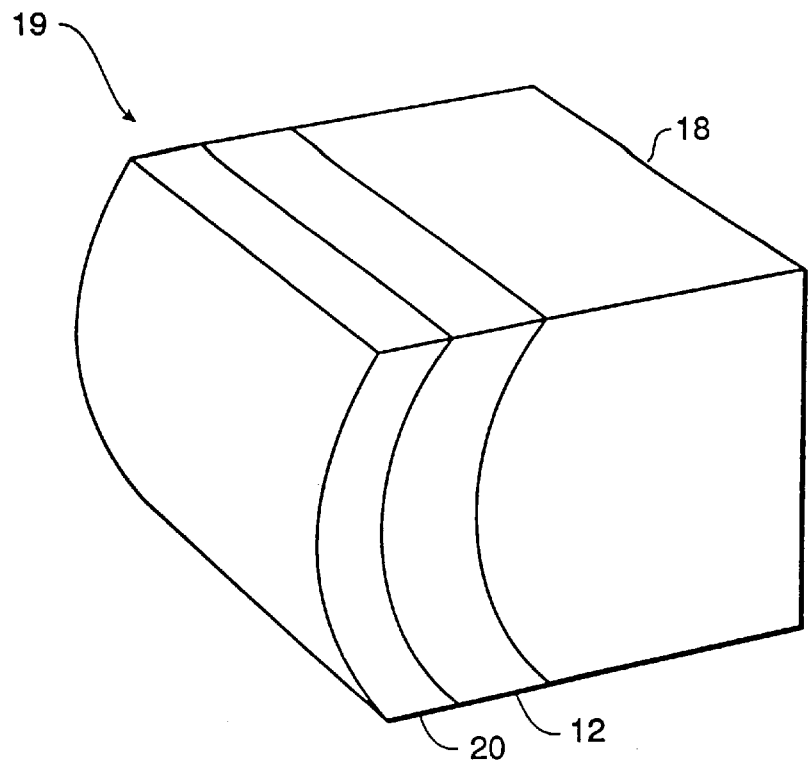
FIG. 4 is a perspective view of another ultrasound transducer in accordance with the present invention.

The ultrasound transducer may also have other shapes, for example, a square shape, as shown in FIG. 4 with like reference numbers labeling like elements.

The acoustic path-length from the periphery of the acoustic elements 12 of the transducers 10 and 19 of FIGS. 3 and 4 are increased relative to the acoustic path-lengths from the centers of the acoustic elements 12. This results in a transducer having a larger focal length than a same sized standard transducer, as explained below.

Figure 11:
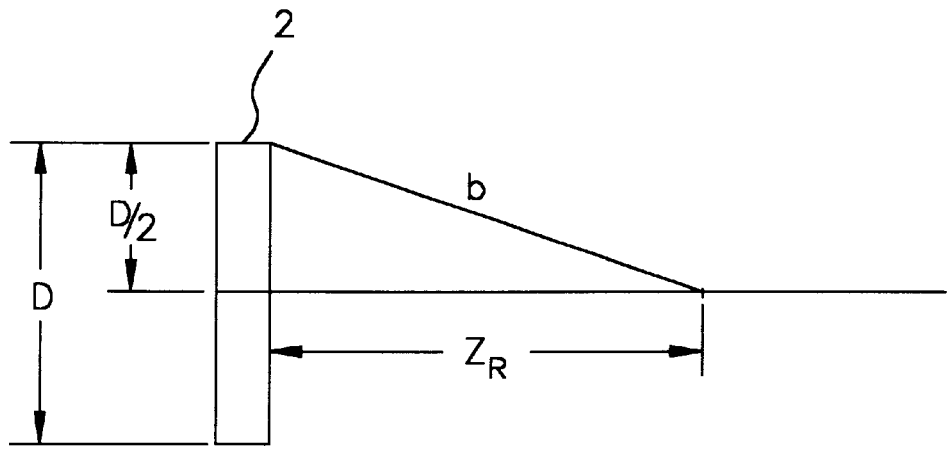
FIG. 11 is a schematic view of a transducer having two opposed flat surfaces and a disk shape.

Although the present invention is not bound by the following theory of operation, it can be determined that the transducer's focal length is mathematically related to the transducer size and shape, the speed of sound in the environment, and the acoustic frequency at which the transducer is operated. The transition length from the near-field to the far-field, $Z_R$, is defined as the distance from the transducer where the difference between the acoustic path-length from the center of the transducer and from the periphery of the transducer is one-half a wavelength (½λ). The focal length $Z_f$ is located at $Z_f \approx 0.8 Z_R$. Therefore, referring to FIG. 11, for a flat-surfaced, cylindrical transducer 2 having a diameter D, the focal length $Z_f$ can be determined:

where c=speed of sound in environment

λ=wavelength $$b - Z_R = \frac{\lambda}{2} \quad (1)$$

$$b = \sqrt{Z_R^2 + \frac{D^2}{4}}, \quad \text{if } Z_R^2 \gg \frac{D^2}{4} \text{ then:}$$

$$b = \sqrt{Z_R^2} + \frac{D^2}{4} \times \frac{1}{2} \times \frac{1}{\sqrt{Z_R^2}} = Z_R + \frac{D^2}{8Z_R}$$

$$\rightarrow \frac{D^2}{8Z_R} = \frac{\lambda}{2} \rightarrow Z_R = \frac{D^2}{4\lambda}$$

$$\rightarrow Z_f \approx 0.8 Z_R = \frac{0.8 D^2}{4\lambda}$$

Figure 12:
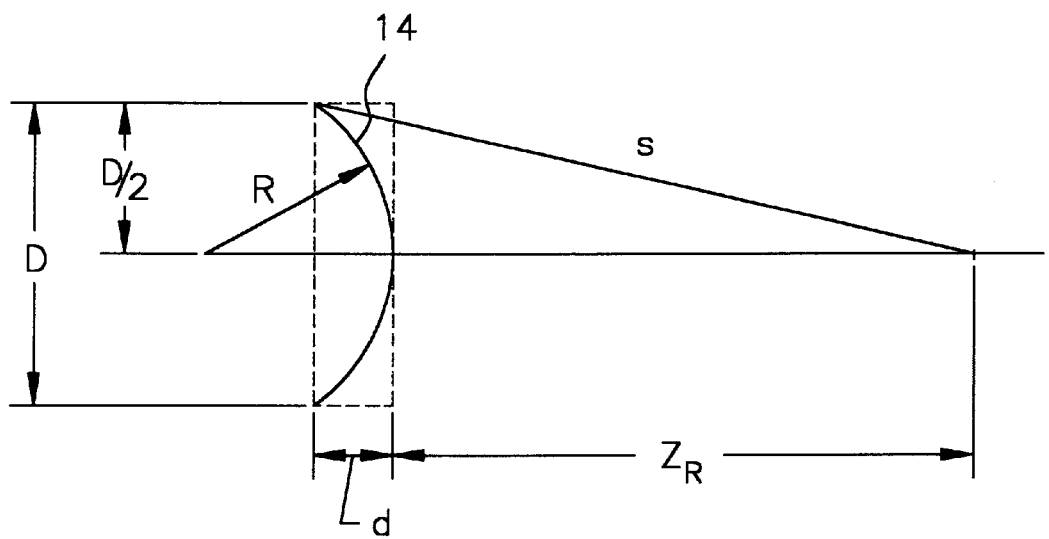
FIG. 12 is a schematic view of a disk-shaped transducer having a convex surface.

Referring now to FIG. 12, a similar analysis may be performed for an acoustic element 12 having a convex surface 14:

where D=transducer diameter

R=transducer convex surface radius f=acoustic frequency

λ=wavelength c=speed of sound in environment $$s - Z_R = \frac{\lambda}{2} \quad (2)$$

$$s = \sqrt{Z_R^2 + \frac{D^2}{4}}; \quad \text{if } Z_R \gg \frac{D^2}{4} \text{ then } s = Z_R + \frac{D^2}{8Z_R}$$

$$d = R - \sqrt{R^2 - \frac{D^2}{4}}; \quad \text{if } R \gg \frac{D^2}{4} \text{ then}$$

$$d = \frac{D^2}{8R} \rightarrow Z_R + \frac{D^2}{8Z_R} - \left(Z_R - \frac{D^2}{8R}\right) - \frac{\lambda}{2}$$

$$\rightarrow \frac{D^2}{8Z_R} = \frac{\lambda}{2} - \frac{D^2}{8R}$$

$$\rightarrow \frac{1}{Z_R} = \frac{4\lambda}{D^2} - \frac{1}{R}$$

$$\rightarrow Z_R = \frac{D^2 R}{4\lambda R - D^2} = \frac{D^2 Rf}{4Rc - D^2 f}$$

$$\left(\text{if } R \rightarrow \infty \text{ then } Z_R = \frac{D^2}{4\lambda} = \frac{D^2 f}{4c}\right)$$

$$Z_R = \frac{D^2 Rf}{4Rc - D^2 f} \rightarrow Z_f \approx 0.8 Z_R = \frac{0.8 D^2 Rf}{4R_c - D^2 f}$$

Hence, the relationship between the focal length and the above parameters for a convex-surfaced cylindrical transducer is expressed by the above equation (2). Looking at FIG. 12, it can be seen that the acoustic path-length from the periphery of the transducer, s, is increased with respect to the acoustic path-length from the center of the transducer to the transition point, $Z'_R$, of a standard transducer. Described in the simplest terms, curving transducer 14 into a convex shape moves the periphery of the transducer distally, while the center of the transducer is fixed, thereby increasing the acoustic path-length from the periphery.

Using the above equation (2), the table of FIG. 14 shows the theoretical calculated focal lengths ($Z_R$ in mm) of a convex-surfaced, cylindrical ultrasound transducer 10 having a convex acoustic element 12 according to the present invention for radii of curvature (radius R) varying from 1 mm to essentially a flat surface (1E+15 mm). The outside diameter (OD) of the acoustic element is 1.9304 mm, the central frequency is 9 megahertz (MHz) and the speed of sound in water/blood is 1540000 mm/s. As the data in the table of FIG. 14 shows, the focal length for a flat acoustic element (R=1E+15) is 5.44 mm. As the radius decreases, the focal length of the transducer increases to a maximum of 58.8 mm at a radius of 6 mm. Therefore, it can be seen that the use of a convex acoustic element 12 increases the focal length and hence also increases the near-field of the ultrasound transducer.

Extending the focus of the transducer permits a small transducer to image from within larger chambers, such as the walls of the heart or large vessels where the features to be imaged are thicker and much further away from the transducer than the walls of small lumen vessels. Therefore, a transducer having a 1.97 mm diameter which can be fit into a minimum catheter size of about 9F can be introduced into organs or large vessels via relatively small, remote vessels. After it is in position, the transducer has a sufficiently extended focal length to image the walls of the organ or large vessels with high resolution and penetration depth.

Figure 5:
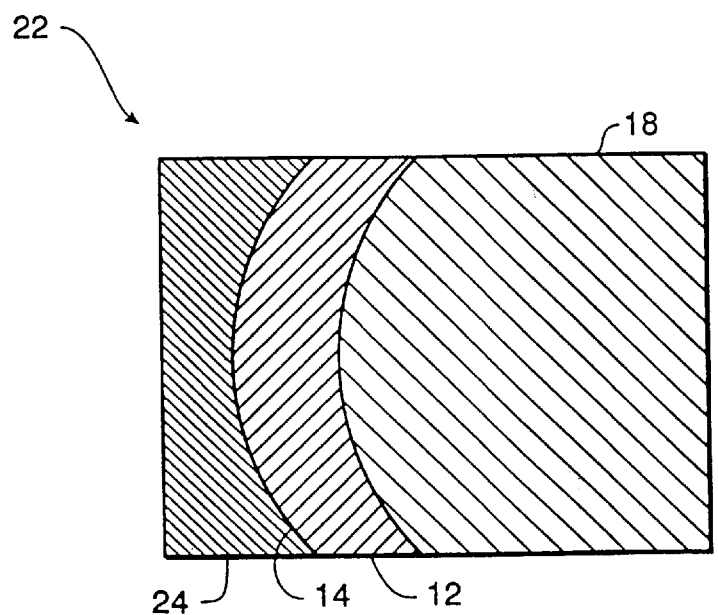
FIGS. 5, 6, 7, 8 and 9 are cross-sectional views of alternative ultrasound transducers in accordance with the present invention.

Referring to FIG. 5, an ultrasound transducer 22 is similar to transducer 10, except that the acoustic matching layer 24 has a flat outer surface 25. Again, the ultrasound transducer 22 has an increased acoustic path-length from the periphery of the acoustic element 12 relative to the acoustic path-length from the center of the acoustic element 12. This results in an extended focus similar to the transducer 10 described above. The nonuniform thickness matching layer 24 may enhance the increase in acoustic path-length from the periphery if the speed of sound in the matching layer 24 is lower than the speed of sound in the medium, or it may diminish the increase in acoustic path-length from the periphery if the speed of sound in the matching layer 24 is greater than the speed of sound in the medium.

Figure 6:
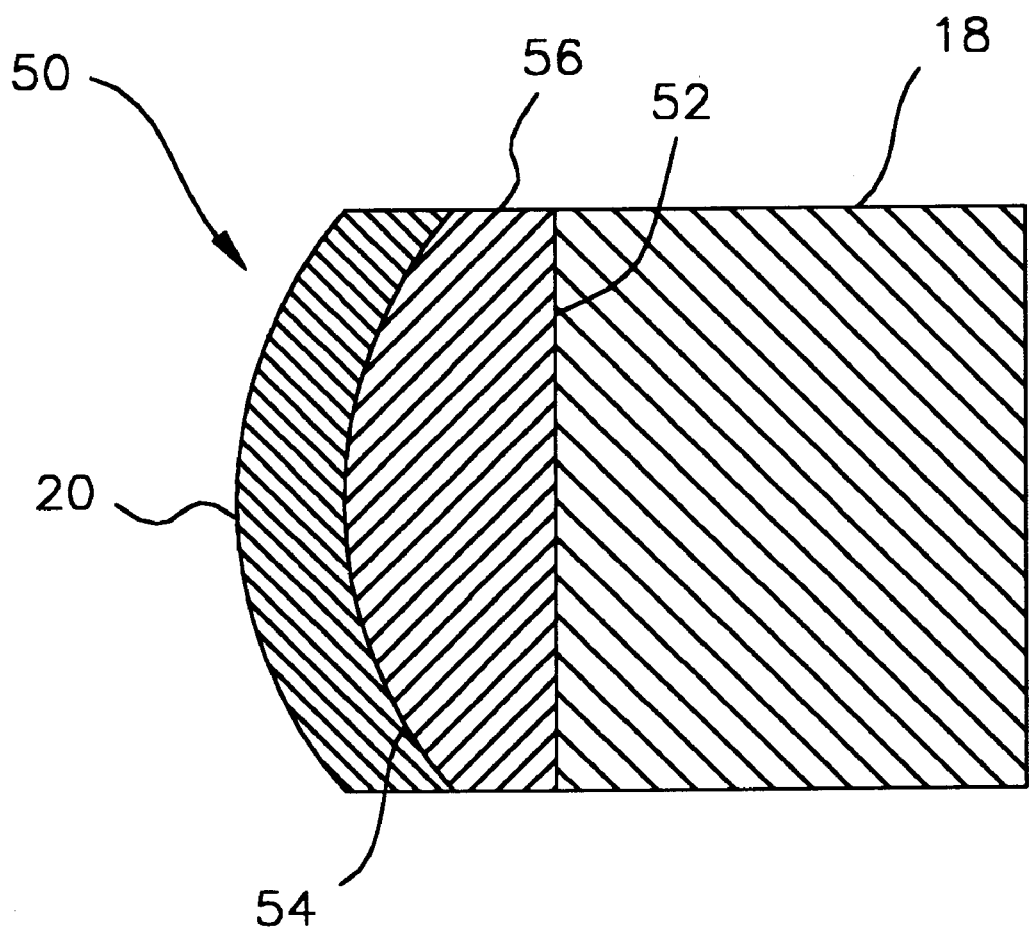
Figure 7:
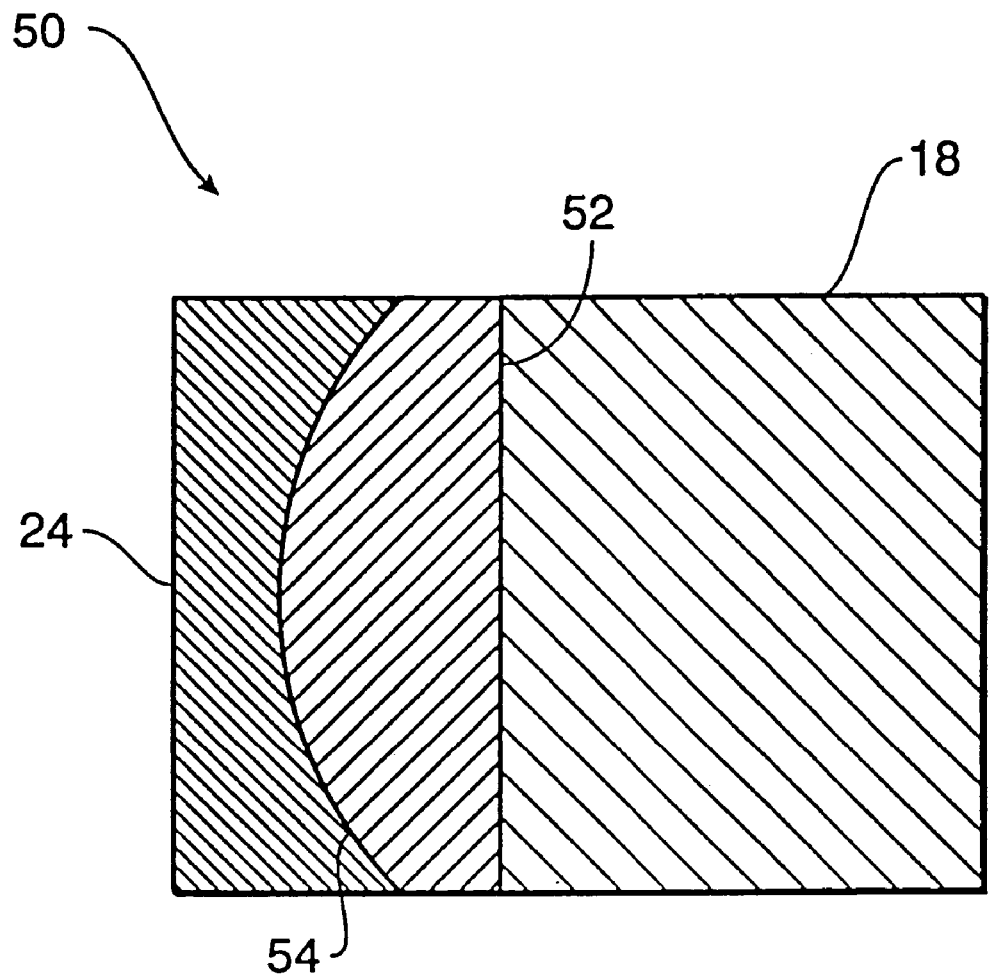

Additional variations of the first described embodiment of FIG. 3a are shown in FIGS. 6 and 7. In these two embodiments, the ultrasound transducer 50 has a flat back side 52 and a convex surface 54 on the front side. It can be seen that the ultrasound transducers 50 of FIGS. 6 and 7 will also increase the acoustic path-length from the periphery of the acoustic element 56 relative to the acoustic path-length from the center of the acoustic element 56. For the transducer of FIG. 7, the nonuniform thickness matching layer 24 will have a similar effect as that described above in reference to the transducer of FIG. 5.

An extended focus can also be achieved for a transducer with a flat-surfaced acoustic element through effecting the acoustic path-lengths by the use of a matching layer having a curved surface such that it functions as a lens. The shape of the curvature depends on the relative speeds of sound in the matching layer material and the environment or medium in which the waves are being transmitted, as discussed below.

Figure 8:
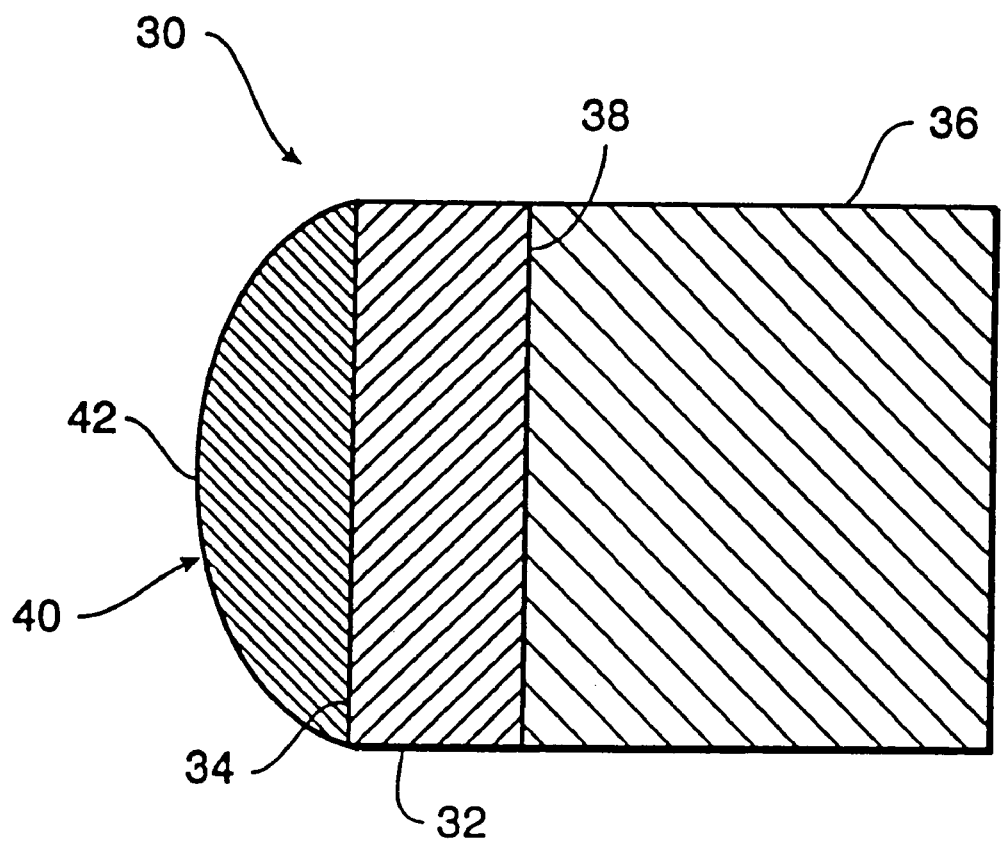

Turning now to FIG. 8, another alternative ultrasound transducer 30 comprises an acoustic element 32 having a flat front side 34 from which ultrasonic waves are transmitted and received. An acoustic backing 36 may be attached to the back side 38 of the acoustic element 32. An acoustic matching layer 40 is laid on the front side 34 of the acoustic element 32. The acoustic matching layer 40 has a convex surface 42 on the side opposite the acoustic element 32. The acoustic matching layer 40, therefore, acts as a lens. The acoustic matching layer 40 is made of a material having an acoustic impedance which is optimized for the environment or medium through which the ultrasound waves travel and the object to be imaged. Those skilled in the art will appreciate this design choice.

Figure 13:
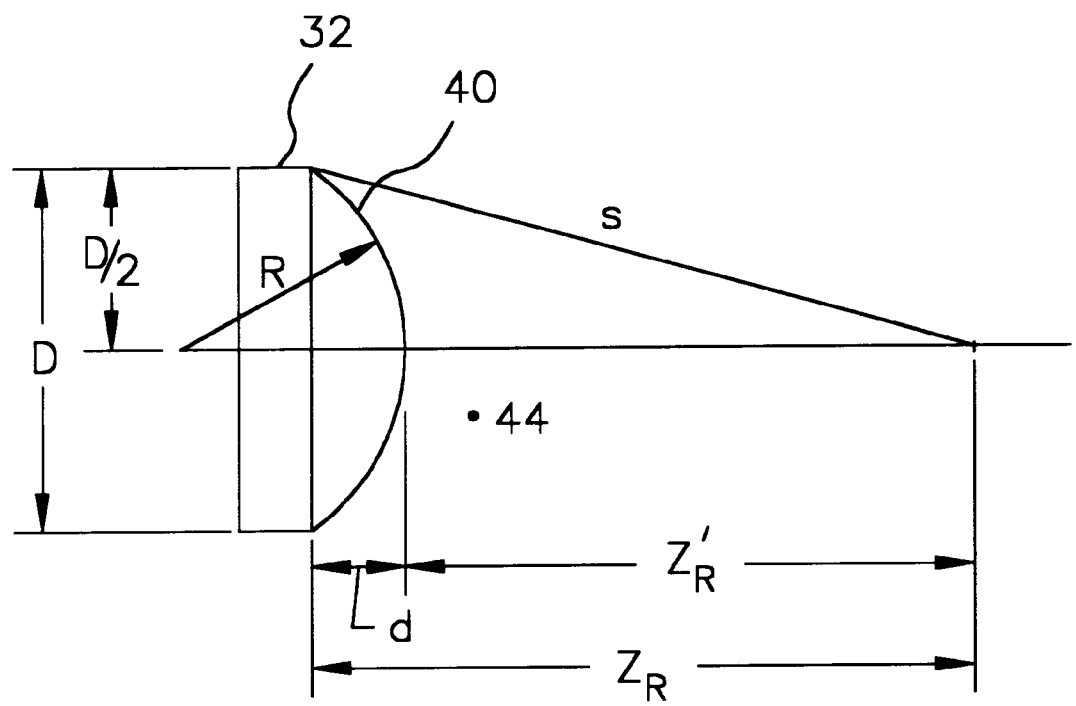
FIG. 13 is a schematic view of a flat, disk-shaped transducer having a flat surface and a convex acoustic matching layer.

In order to produce a transducer having an extended focus, the acoustic matching layer 40 material must be chosen so that the speed of sound in the acoustic matching layer 40 is greater than the speed of sound in the environment or medium. In this way, the acoustic path-length from the center of the acoustic element 32 is decreased relative to the acoustic path-length from the periphery. A list of various materials and their corresponding density ($\rho$) and speed of sound ($V_L$) is shown in FIGS. 20a–f. Then, referring to FIG. 13, the theoretical focal length can be determined:

where $c_1$=speed of sound in lens medium 40

$c_2$=speed of sound in environment 44

D=diameter of convex-surfaced acoustic matching layer (lens)

f=acoustic frequency

R=convex lens radius $$d = R - \sqrt{R^2 - \frac{D^2}{4}} \text{, if } R^2 \gg \frac{D^2}{4} \text{then} \quad (3)$$

$$d = R - \left(\sqrt{R^2 - \frac{D^2}{4}} \frac{1}{2\sqrt{R^2}}\right) = \frac{D^2}{8R}$$

$$s = \sqrt{Z_R^2 + \frac{D^2}{4}} \text{ ; if } Z_R^2 \gg \frac{D^2}{4} \text{then } s = Z_R + \frac{D^2}{8Z_R}$$

$$\frac{S}{\lambda_2} - \frac{Z_R}{\lambda_2} - \frac{d}{\lambda_1} = \frac{1}{2}$$

$$\rightarrow \left(Z_R + \frac{D^2}{8Z_R}\right)\frac{f}{c_2} - \left(Z_R - \frac{D^2}{8R}\right)\frac{f}{c_2} - \frac{D^2}{8R}\frac{f}{c_1}$$

$$= \frac{1}{2}$$

$$D^2 \frac{f}{8Z_R C_2} + \frac{D^2 f}{8RC_2} - \frac{D^2 f}{8RC_1} = \frac{1}{2}$$

$$\rightarrow \frac{1}{Z_R} + \frac{1}{R} - \frac{C_2}{RC_1} = \frac{4C_2}{D^2 f}$$

$$\rightarrow \frac{1}{Z_R} = \frac{4C_2 RC_1 + D^2 fC_2 - D^2 fC_1}{D^2 fRC_1}$$

$$Z_R = \frac{D^2 fRC_1}{4RC_1 C_2 + D^2 f(C_2 - C_1)}$$

The table of FIG. 15 shows the calculated focal lengths ($Z_R$) for lenses of varying radii for the ultrasound transducer 30 having a flat acoustic element 32 and an acoustic matching layer 40 having a convex surface 42. The outside diameter (OD) of the acoustic element 32 and acoustic matching layer 40 is 1.9304 mm, the central frequency is 9 MHz, the speed of sound in the acoustic matching layer is 2,000,000 mm/s and the speed of sound in the medium (water/blood) is 1,540,000 mm/s. A maximum focal length of 14.56 mm is found for a radius of 2 mm compared to a focal length of 5.44 mm for an essentially flat acoustic matching layer (R=1E+15 mm). Thus, the convex acoustic matching layer (which also acts as a lens) can be seen to extend the focal length of the ultrasound transducer 30.

Figure 16:
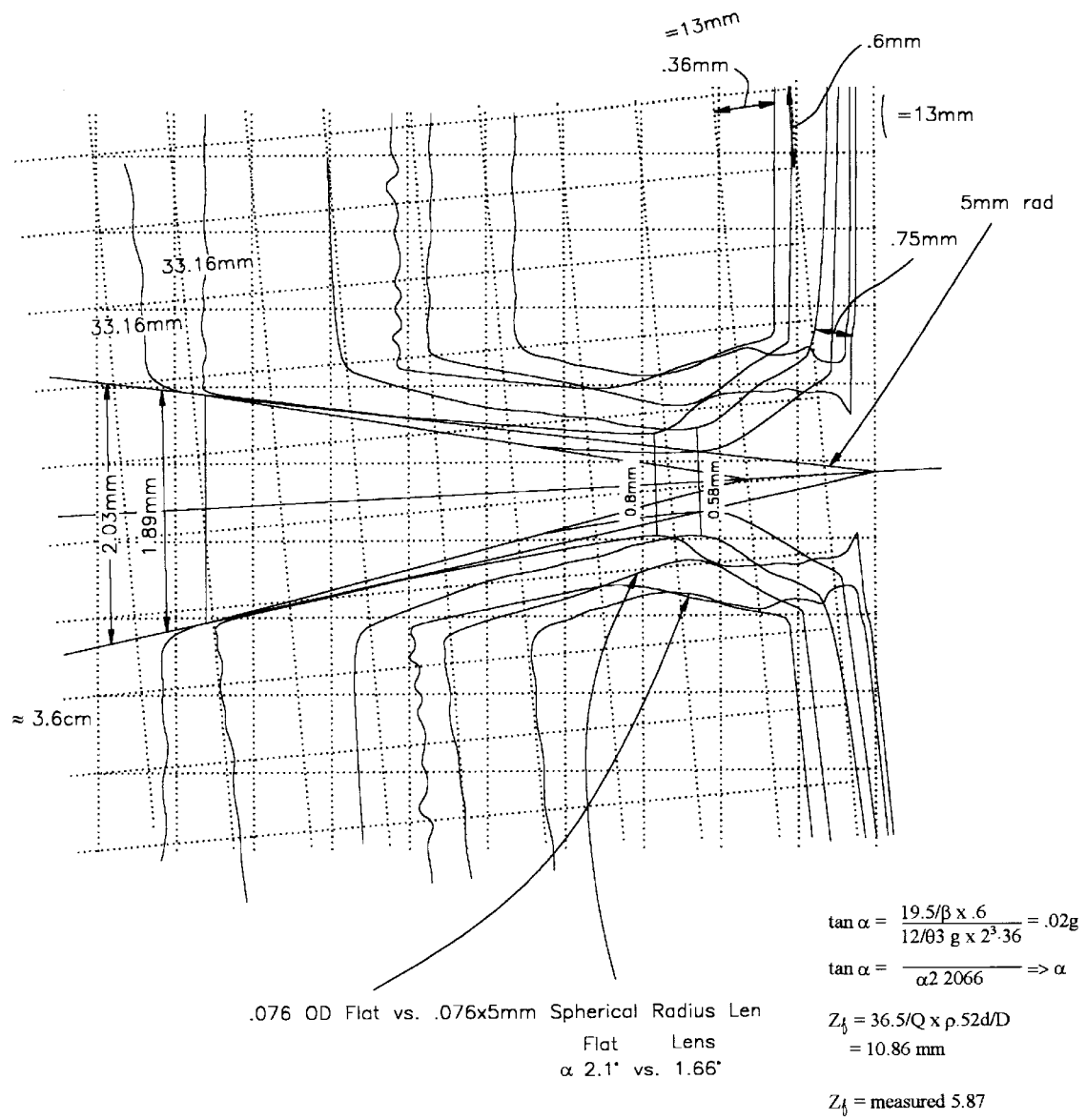
FIG. 16 is an energy plot comparing an ultrasound transducer having a flat acoustic element and a flat acoustic matching layer to an ultrasound transducer having a flat acoustic element and a spherical radius acoustic matching layer.

FIG. 16 shows an empirical test comparing an ultrasound transducer having a flat acoustic element and a flat acoustic matching layer to an ultrasound transducer having a flat acoustic element and a spherical radius acoustic matching layer (lens). The focal point is located at the point where the energy lines converge. As is shown in FIG. 16, the focal length of the ultrasound transducer having the lens (0.8 mm) is longer than the ultrasound transducer without the lens (0.6 mm).

Figure 19:
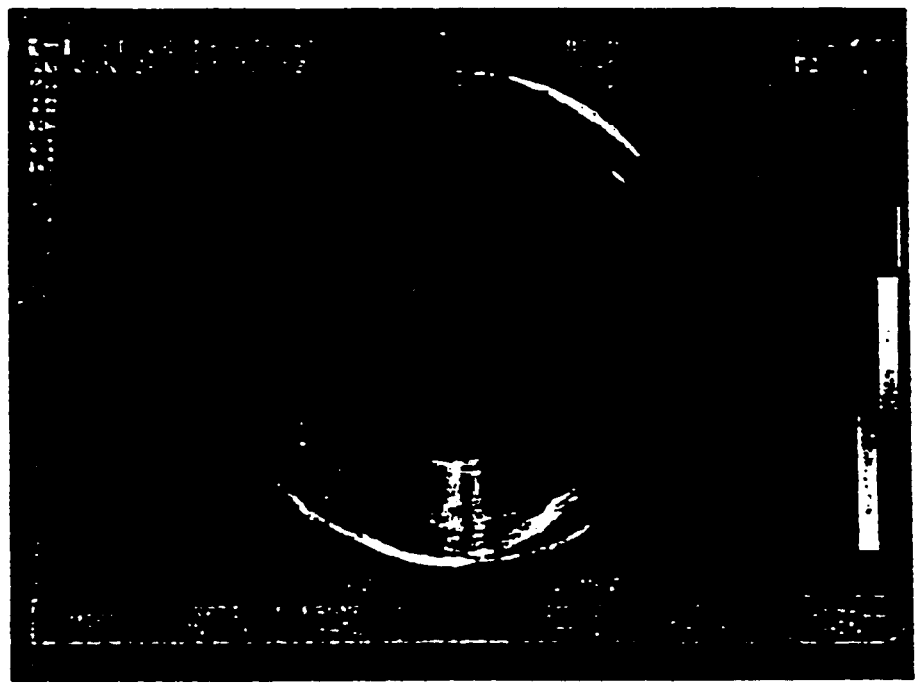
FIG. 19 is an ultrasound image from a lateral resolution experiment.

Lateral resolution experiments indicate that a convex matching layer improves lateral resolution. FIG. 19 is an image produced by an ultrasound transducer having a 0.076" outer diameter and a 5 mm radius lens operating at a central frequency of 9 $MH_z$. A pair of wires 5 mm apart could be resolved at a distance of 4.0–4.5 cm from the transducer.

Figure 9:
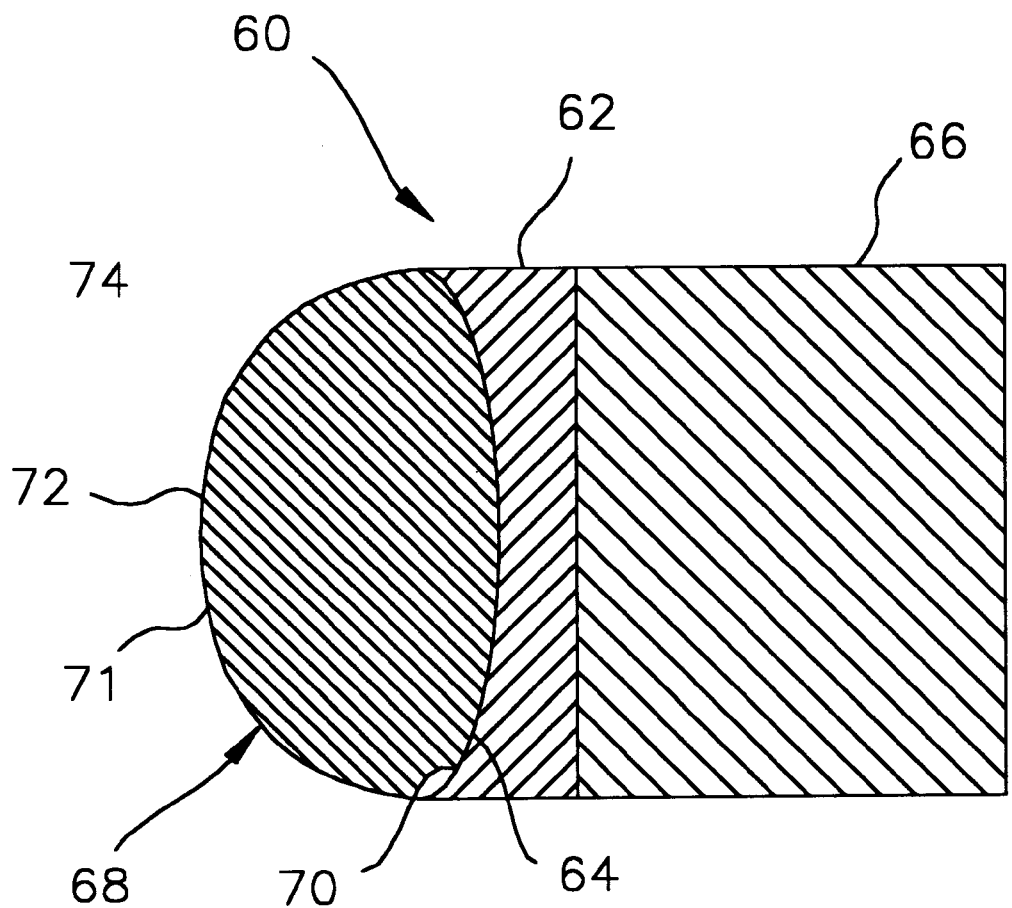

FIG. 9 shows yet another embodiment of an ultrasound transducer 60 according to the present invention. The ultrasound transducer 60 comprises an acoustic element 62 having a concave surface 64 on the front side. An acoustic backing 66 is attached to a side of the acoustic element opposite the concave surface 64. A matching layer 68 is laid on the concave surface 64 of the acoustic element 62. The back side of the matching layer 68 has a convex surface 70 which matches the concave surface 64 of the acoustic element 62 and a concave surface 72 on its front side. The concave surface 72 of the matching layer 68 must be such that the acoustic path-length from the center of acoustic element 62 is decreased relative to the acoustic path-length from the periphery of the acoustic element 62. For this to occur, the speed of sound in the matching layer 68 must be greater than the speed of sound in the environment or medium 74 surrounding the matching layer 68. This can be understood by considering that the periphery of a transmitted wave will exit the convex surface of the acoustic matching layer 68 and enter the medium first, while the center of the transmitted wave will exit the convex surface of the matching layer 68 and enter the medium at a later time, but at a further distance. Therefore, the acoustic path-length at the center of the transducer 62 will be decreased relative to the acoustic path-length of the periphery (because the speed of sound in the medium 74 is slower than the speed of sound in the acoustic matching layer 68). The appropriate material may be chosen from the tables of FIGS. 20a–f listing the density (ρ) and speed of sound for a variety of materials. For example, the speed of sound in silver epoxy is approximately 2.01–2.15 mm/$\mu$sec which is greater than the speed of sound in water/blood (1.5 mm/$\mu$sec). Therefore, silver epoxy would be an appropriate material for a convex lens according to the present invention.

Figure 10:
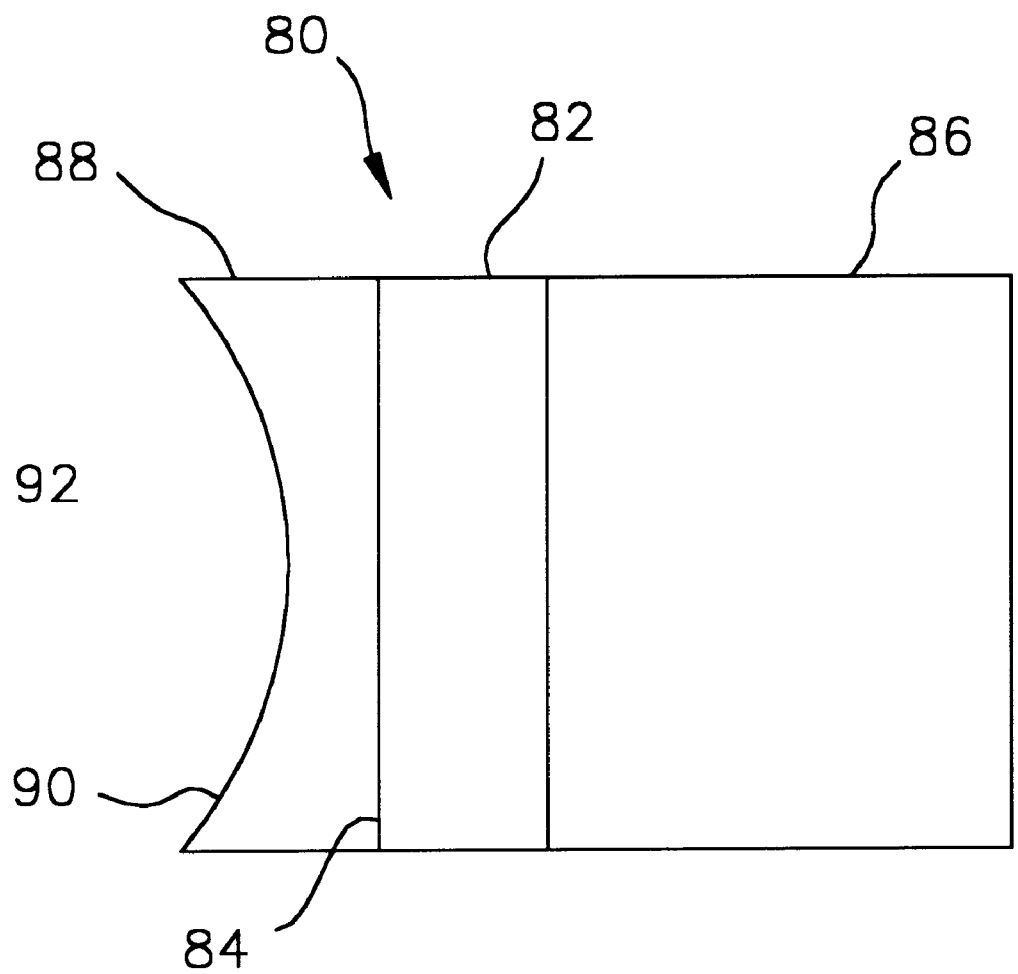
FIG. 10 is a cross-sectional view of an ultrasound transducer in accordance with the present invention.

Turning to FIG. 10, still another embodiment of an ultrasound transducer 80 according to the present invention is shown. The ultrasound transducer 80 comprises an acoustic element 82 having a flat surface 84 on the front side. An acoustic backing 86 is attached to the back side of the acoustic element 82. An acoustic matching layer 88 is laid on the front side of the acoustic element 82. The acoustic matching layer 88 has a concave surface 90 on the side opposite the acoustic element 82. The acoustic matching layer 88 acts as a lens.

In order to configure the transducer 80 with an extended focus, the acoustic matching layer 88 is made of a material in which the speed of sound is less than the speed of sound in the intended medium 92. Hence, the convex acoustic matching layer 88 results in an acoustic path-length from the periphery of the acoustic element 82 is increased relative to the acoustic path-length from the center. As an example, for a medium consisting of blood/water (speed of sound 1.54 mm/$\mu$sec), an appropriate material may be chosen from FIGS. 20a–f, such as any suitable RTV which have listed speeds of sound ranging from 0.67 mm/$\mu$sec to 1.11 mm/$\mu$sec.

Figure 17:
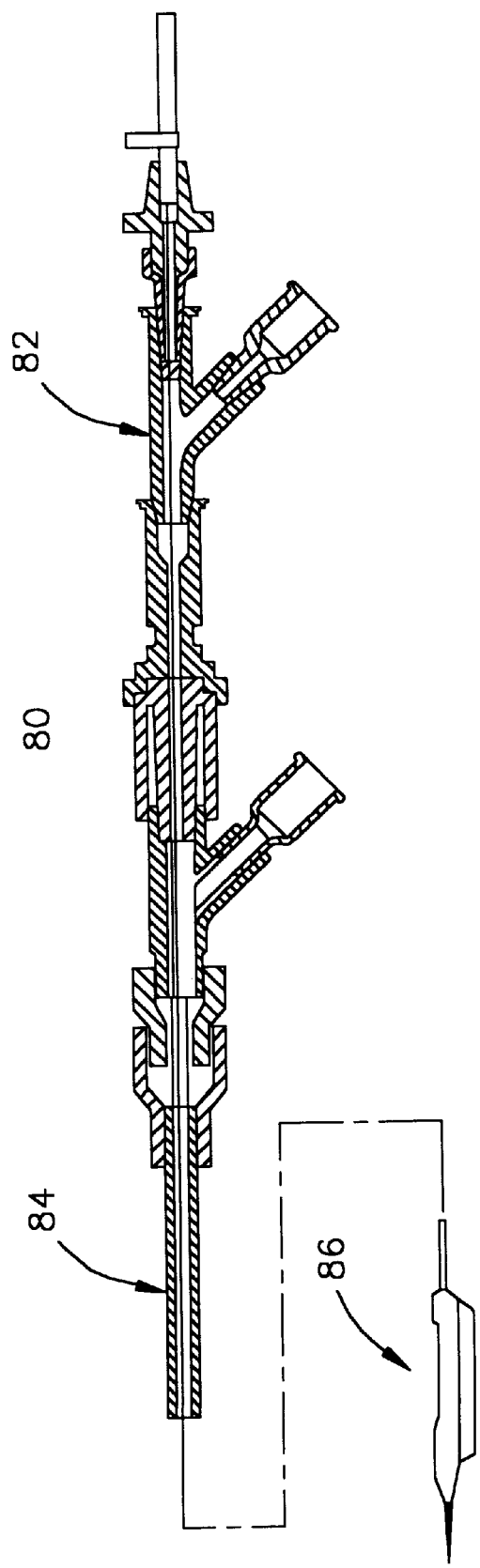
FIG. 17 is a cross-sectional view of an ultrasound imaging catheter in which the ultrasound transducer of the present invention may be used.

In another aspect of the present invention, the ultrasound transducers described above may be carried by an ultrasound imaging catheter as described in Yock, U.S. Pat. No. 5,313,949, Crowley et al., U.S. Pat. No. 4,951,677, and Pomeranz, U.S. Pat. No. 5,095,911. These patents and all other patents listed herein are hereby incorporated by reference. As an example, FIG. 17 shows an atherectomy ultrasound imaging catheter 80 having a proximal end 82 and a distal end 84. The distal end 84 has a transducer system 86 into which is mounted the ultrasound transducer (not shown), such as those described herein.

Figure 18:
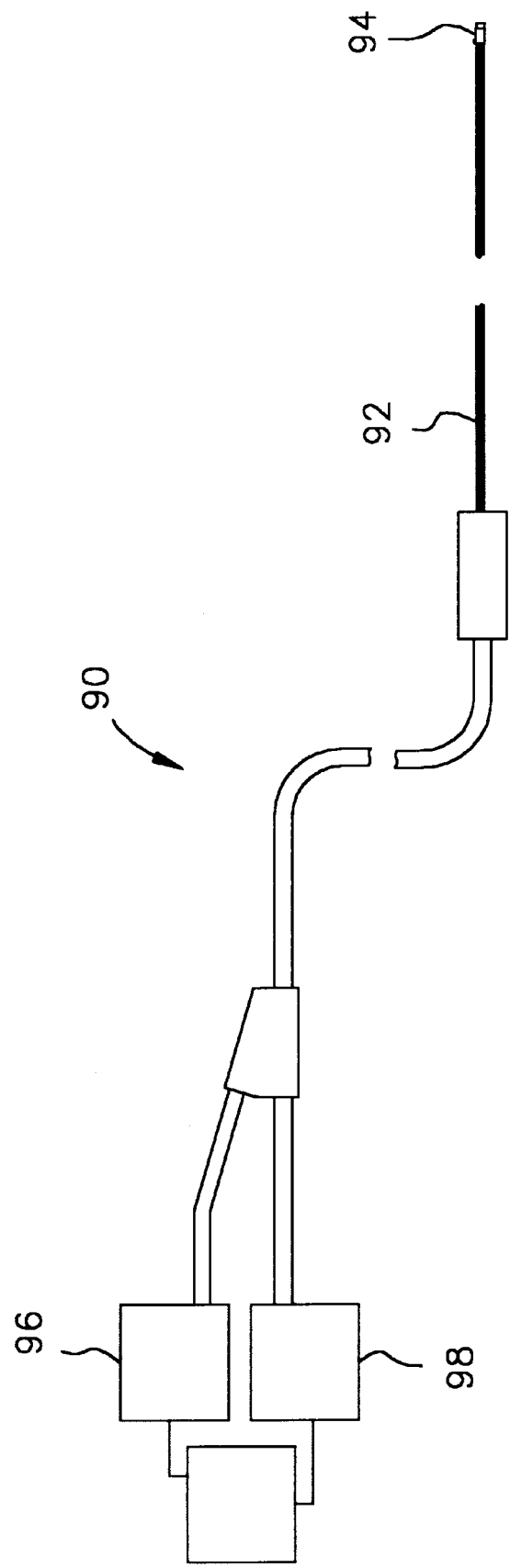
FIG. 18 is a schematic representation of an imaging guidewire in which the ultrasound transducer of the present invention may be used.

In another embodiment, the ultrasound transducer of the present invention may be implemented into an imaging guidewire as is known in the art and described in Sieben, U.S. Pat. No. 5,353,798. FIG. 18 illustrates an imaging guidewire 90 having a schematic representation of a characteristic elongate member 92 which includes a sensor assembly 94 at its distal end. A signal processing unit 96 and control unit 98 are disposed at the proximal end of the imaging guidewire 90. The ultrasound transducer (not shown) is housed in the sensor assembly 94.

While the above description contains many specifics, these should not be construed as limitations on the scope of the invention, but rather as examples of particular embodiments thereof. Accordingly, the invention is not to be limited to the particular forms disclosed, but rather, the invention is to cover all modifications, equivalents, and alternatives falling within the spirit and scope of the appended claims.

What is claimed is:

1. An ultrasound transducer comprising:
   an acoustic element for transmitting and receiving ultrasound waves, said acoustic element having a convex outer surface on a side which transmits and receives ultrasound waves;
   an acoustic backing layer attached to a back side of said acoustic element opposite the side of said acoustic element having a convex surface; and
   an acoustic matching layer having a first side attached to the acoustic element on the side of said acoustic element having a convex surface and a second side defining an outer surface;
   wherein a side of said acoustic backing layer attached to the back side of said acoustic element is substantially flat and the back side of said acoustic element is substantially flat.

2. The ultrasound transducer of claim 1, wherein said acoustic matching layer has a thickness of substantially one quarter wavelength.

3. An ultrasound transducer comprising:
   an acoustic element having a side that transmits and receives ultrasound waves;
   an acoustic backing element attached to a side of said acoustic element opposite said side of said acoustic element that transmits and receives ultrasound waves; and
   an acoustic matching layer attached to the acoustic element on the side of said acoustic element that transmits and receives ultrasound waves, said acoustic matching layer having a convex outer surface on a side opposite the side attached to said acoustic element;
   wherein said acoustic element has a concave surface on the side that transmits and receives ultrasound waves.

4. An ultrasound transducer comprising:
   an acoustic element for generating ultrasound waves, a backing element attached to a back side of said acoustic element, and a matching layer attached to a transmitting and receiving side of said acoustic element for matching said element to a preselected medium at a predetermined frequency;

said transmitting and receiving side of said acoustic element having a convex shape and having a radius of curvature large enough to maintain a positive focal length ($Z_f$) within said preselected medium at said predetermined frequency of operation.

5. The ultrasound transducer of claim 4, wherein said matching layer has a thickness of substantially one quarter wavelength of an ultrasound wave at said predetermined frequency of operation.

6. An ultrasound transducer comprising:

an acoustic element for generating ultrasound waves, a backing element attached to a back side of said acoustic element, and a matching layer having a first side attached to a transmitting and receiving side of said acoustic element and a second side opposite said first side;

said transmitting and receiving side of said acoustic element being substantially flat, said matching layer being formed from a material having an acoustic transmission velocity greater than an acoustic transmission velocity of a preselected medium, and said second side of said matching layer having a convex shape and having a radius of curvature large enough to maintain a positive focal length ($Z_f$) for said ultrasound transducer within said preselected medium at a predetermined frequency of operation.

7. An ultrasound transducer comprising:

an acoustic element, a backing layer attached to one side of said acoustic element, and a matching layer attached to a transmitting and receiving side of said acoustic element for matching said element to a predetermined medium at a predetermined frequency;

said acoustic element and matching layer being configured to maximize a transition length of said ultrasound transducer while maintaining a substantially conventional near field to far field beam transition pattern with a minimum beam width located substantially at a focal length of said transducer, when said transducer is operated within said predetermined medium and at said predetermined operating frequency.

8. The ultrasound transducer of claim 7, wherein said transmitting and receiving surface of said acoustic element has a convex shape.

9. The ultrasound transducer of claim 7, wherein said transmitting and receiving surface of said acoustic element is substantially flat, said matching layer is formed from a material having an acoustic transmission velocity greater than an acoustic transmission velocity of said predetermined medium, and said matching layer has a side opposite a side attached to said transmitting and receiving surface of said acoustic element, said opposite side having a convex shape.

10. The ultrasound transducer of claim 7, wherein said transmitting and receiving surface of said acoustic element is substantially flat, said matching layer is formed from a material having an acoustic transmission velocity slower than an acoustic transmission velocity of said predetermined medium, and said matching layer has a side opposite a side attached to said transmitting and receiving surface of said acoustic element, said opposite side having a concave shape.

11. An ultrasound transducer comprising:

an acoustic element having a substantially circular cross-section and having an outside diameter of substantially 2.0 mm or less, said acoustic element having a back side and a transmitting and receiving side;

a backing layer attached to said back side of said acoustic element; and a matching layer attached to said transmitting and receiving side of said acoustic element;

said acoustic element and said matching layer being configured such that said ultrasound transducer has a transition length not less than substantially 7.5 mm when said ultrasound transducer is operated within a medium having acoustic transmission characteristics similar to human blood and is operated at a frequency between 6.5 MHz and 11.5 MHz.

12. The ultrasound transducer of claim 11, wherein said transmitting and receiving surface of said acoustic element has a convex shape.

13. The ultrasound transducer of claim 11, wherein said transmitting and receiving surface of said acoustic element is substantially flat, said matching layer is formed from a material having an acoustic transmission velocity greater than an acoustic transmission velocity of said predetermined medium, and said matching layer has a side opposite a side attached to said transmitting and receiving surface of said acoustic element, said opposite side having a convex shape.

14. The ultrasound transducer of claim 11, wherein said transmitting and receiving surface of said acoustic element is substantially flat, said matching layer is formed from a material having an acoustic transmission velocity slower than an acoustic transmission velocity of said predetermined medium, and said matching layer has a side opposite a side attached to said transmitting and receiving surface of said acoustic element, said opposite side having a concave shape.

15. An ultrasound transducer comprising:

an acoustic element for generating ultrasound waves, a backing element attached to a back side of said acoustic element, and a matching layer attached to a transmitting and receiving side of said acoustic element for matching said element to a preselected medium at a predetermined frequency;

wherein a ratio of an acoustic path length to a geometric path length from a periphery of said transmitting and receiving side of said acoustic element exceeds a ratio of an acoustic path length to a geometric path length from a center of said transmitting and receiving side of said acoustic element, and wherein said transducer has a positive focal length ($Z_f$) when operated within said preselected medium and at said predetermined frequency.

16. The ultrasound transducer of claim 15, wherein said matching layer has a side having a convex shape opposite a side attached to said transmitting and receiving side of said acoustic element, and wherein a composition of said matching layer is selected such that a velocity of an ultrasound wave transmitted by said acoustic element is greater within said matching layer than in said preselected medium.

17. The ultrasound transducer of claim 16, wherein said transmitting and receiving side of said acoustic element is substantially flat.

18. The ultrasound transducer of claim 16, wherein said transmitting and receiving side of said acoustic element has a concave shape.

19. The ultrasound transducer of claim 16, wherein said transmitting and receiving side of said acoustic element has a convex shape.

20. The ultrasound transducer of claim 15, wherein said matching layer has a side having a concave shape opposite a side attached to said transmitting and receiving side of said acoustic element, and wherein a composition of said matching layer is selected such that a velocity of an ultrasound wave transmitted by said acoustic element is slower within said matching layer than in said preselected medium.

21. The ultrasound transducer of claim 20, wherein said transmitting and receiving side of said acoustic element is substantially flat.

22. The ultrasound transducer of claim 20, wherein said transmitting and receiving side of said acoustic element has a concave shape.

23. The ultrasound transducer of claim 20, wherein said transmitting and receiving side of said acoustic element has a convex shape.

24. The ultrasound transducer of claim 15, wherein said acoustic element of said ultrasound transducer has an outside diameter of no more than substantially 2.0 mm, and said ultrasound transducer has a focal length of no less than substantially 7.5 mm when operated within a medium have acoustic transmission characteristics similar to human blood and is operated at a frequency between 6.5 MHz and 11.5 MHz.

* * * * *